US012807995B2

(12) United States Patent
Taniguchi et al.

(10) Patent No.: US 12,807,995 B2
(45) Date of Patent: Nov. 24, 2026

(54) SENSITIVE DETECTION METHOD FOR UNDIFFERENTIATED MARKER GENES

(71) Applicants: Public University Corporation Yokohama City University, Kanagawa (JP); Eiken Kagaku Kabushiki Kaisha, Tokyo (JP)

(72) Inventors: Hideki Taniguchi, Yokohama (JP); Keisuke Sekine, Yokohama (JP); Ryota Yasui, Tochigi (JP); Atsuka Matsui, Tochigi (JP)

(73) Assignees: Public University Corporation Yokohama City University, Kanagawa (JP); Eiken Kagaku Kabushiki Kaisha, Tokyo (JP)

( * ) Notice: Subject to any disclaimer, the term of this patent is extended or adjusted under 35 U.S.C. 154(b) by 1079 days.

(21) Appl. No.: 17/776,997

(22) PCT Filed: Nov. 12, 2020

(86) PCT No.: PCT/JP2020/042210
§ 371 (c)(1),
(2) Date: Sep. 23, 2022

(87) PCT Pub. No.: WO2021/095798
PCT Pub. Date: May 20, 2021

(65) Prior Publication Data

US 2023/0257813 A1 Aug. 17, 2023

(30) Foreign Application Priority Data

Nov. 15, 2019 (JP) ................................ 2019-207004

(51) Int. Cl.
*C12Q 1/6881* (2018.01)

(52) U.S. Cl.
CPC ..... *C12Q 1/6881* (2013.01); *C12Q 2600/158* (2013.01)

(58) Field of Classification Search
CPC ........................ C12Q 1/6881; C12Q 2600/158
See application file for complete search history.

(56) References Cited

U.S. PATENT DOCUMENTS

| | | | | |
|---|---|---|---|---|
| 2003/0224411 | A1* | 12/2003 | Stanton ................ | C12Q 1/6876 435/6.16 |
| 2012/0070896 | A1 | 3/2012 | Yamanaka et al. | |
| 2014/0243227 | A1 | 8/2014 | Clevers et al. | |
| 2016/0122803 | A1 | 5/2016 | Meissner et al. | |

FOREIGN PATENT DOCUMENTS

| | | | | |
|---|---|---|---|---|
| CN | 103602761 | A | 2/2014 | |
| JP | 2012-527888 | A | 11/2012 | |
| JP | 2014-516562 | A | 7/2014 | |
| JP | 2016-532435 | A | 10/2016 | |
| JP | 2019-162054 | A | 9/2019 | |
| KR | 10-2018-0124619 | A | 11/2018 | |
| WO | 00/28082 | A1 | 5/2000 | |
| WO | WO-2014200905 | A2 * | 12/2014 | ........... C12Q 1/6876 |
| WO | 2015/195949 | A2 | 12/2015 | |
| WO | 2018/135288 | A1 | 7/2018 | |
| WO | WO2021095798 | * | 5/2021 | ........... C12Q 1/6881 |

OTHER PUBLICATIONS

WO2018135288 translated document, Jul. 26, 2018.*
Mol. BioSyst., 10, 970, 1-34 (Year: 2014).*
Biosensor and Bioelectronics, 64: 196-211 (Year: 2015).*
Yasui et al., Stem Cell Reviews and Reports, 18: 2995-3007, Epub Jun. 3, 2022.*
Office Action (with partial translation) dated Nov. 1, 2023, issued in corresponding Chinese Patent Application No. 202080078492.X.
International Search Report issued in corresponding International Patent Application No. PCT/JP2020/042210 dated Jan. 12, 2021.
English translation of International Preliminary Report on Patentability issued May 17, 2022, in PCT International Application No. PCT/JP2020/042210.
Pandy et al. "Reverse transcription loop mediated isothermal amplification (RT-LAMP), a light for mammalian transcript analysis in low input laboratories," Journal of Cellular Biochemistry, 119 (6): 4334-4338 (2018).
Wu et al., "Strand displacement amplification for ultrasensitive detection of human pluripotent stem cells," Analytica Chimica Acta, 881: 124-130 (2015).

(Continued)

*Primary Examiner* — Cynthia B Wilder
(74) *Attorney, Agent, or Firm* — Morgan, Lewis & Bockius LLP

(57) ABSTRACT

The present invention provides a sensitive and simple detection method, and a kit therefor, which detects residual undifferentiated human pluripotent stem cells in an intermediate product and/or a final product of a regenerative medical products, using an isothermal nucleic acid amplification method, and specifically, a LAMP method. A method for detecting presence or absence of undifferentiated cells in a non-undifferentiated cell population, wherein RNA derived from an undifferentiation marker gene exhibiting a significant difference in expression level between the undifferentiated cells and the non-undifferentiated cells in a sample containing a nucleic acid derived from the cell population of interest is detected by the isothermal nucleic acid amplification method. The kit for detecting presence or absence of undifferentiated cells in a non-undifferentiated cell population comprises a reagent with which RNA derived from an undifferentiation marker gene exhibiting a significant difference in expression level between the undifferentiated cells and the non-undifferentiated cells is detected by the isothermal nucleic acid amplification method.

22 Claims, 6 Drawing Sheets

Specification includes a Sequence Listing.

(56) References Cited

OTHER PUBLICATIONS

Yasui et al., "Highly Sensitive Detection of Human Pluripotent Stem Cells by Loop Mediated Isothermal Amplification," Stem Cell Reviews and Reports, 18 (3): 2995-3007 (2022).
Extended European Search Report issued in European Patent Application No. 20888670.5 dated Dec. 5, 2023.

* cited by examiner

[Fig. 1]
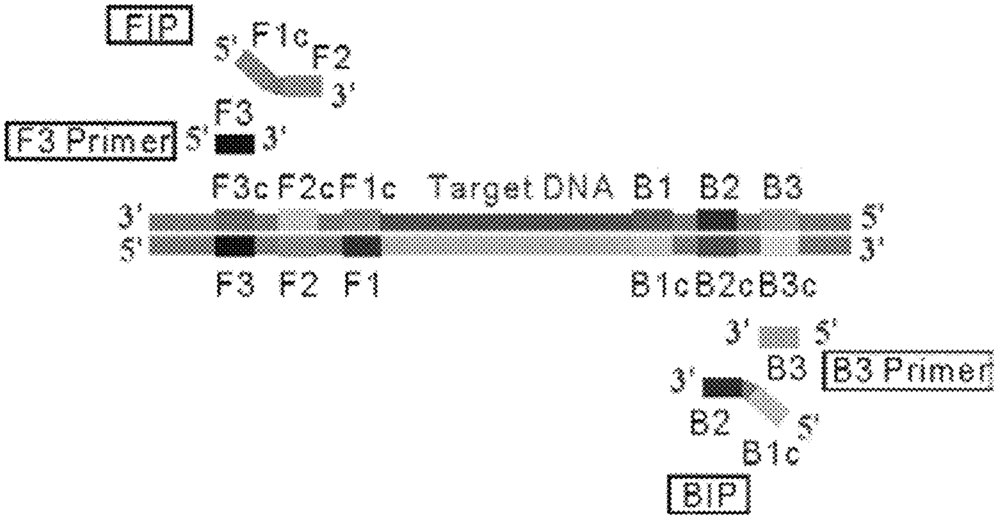

[Fig. 2]
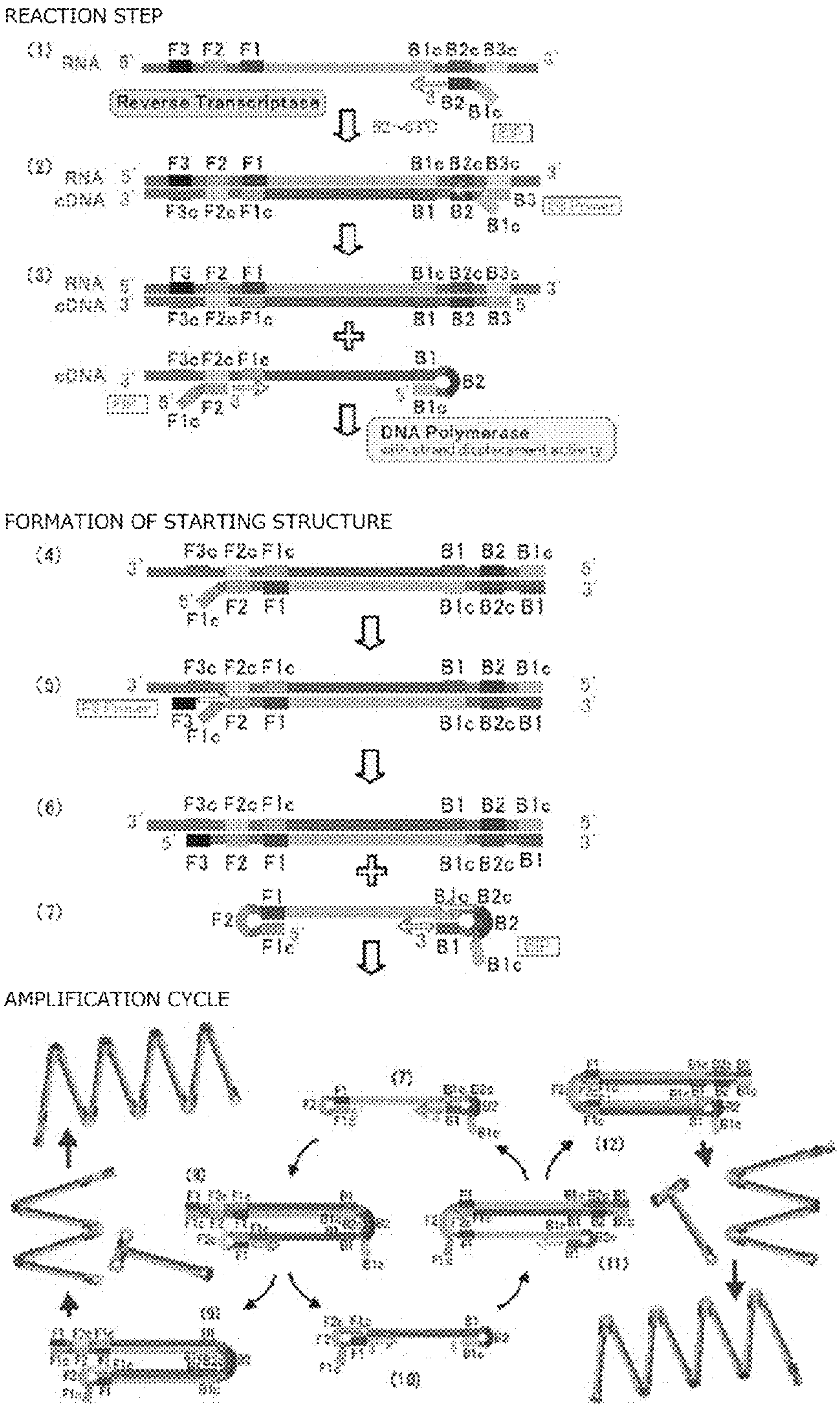

[Fig. 3]
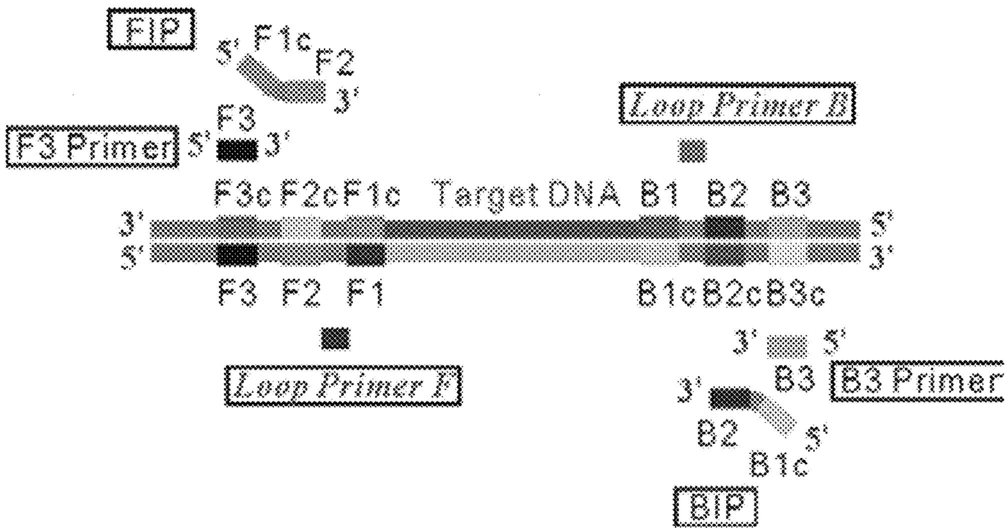

[Fig. 4(a)]
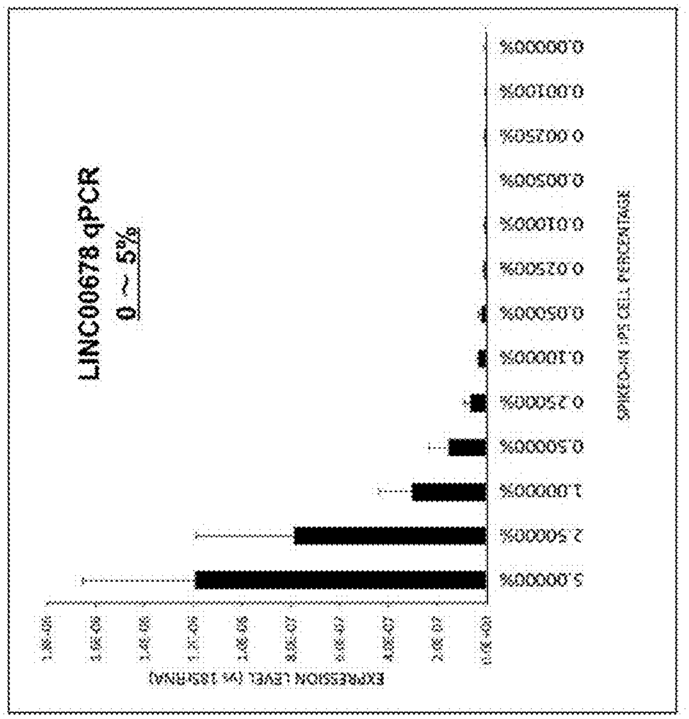
[Fig. 4(b)]
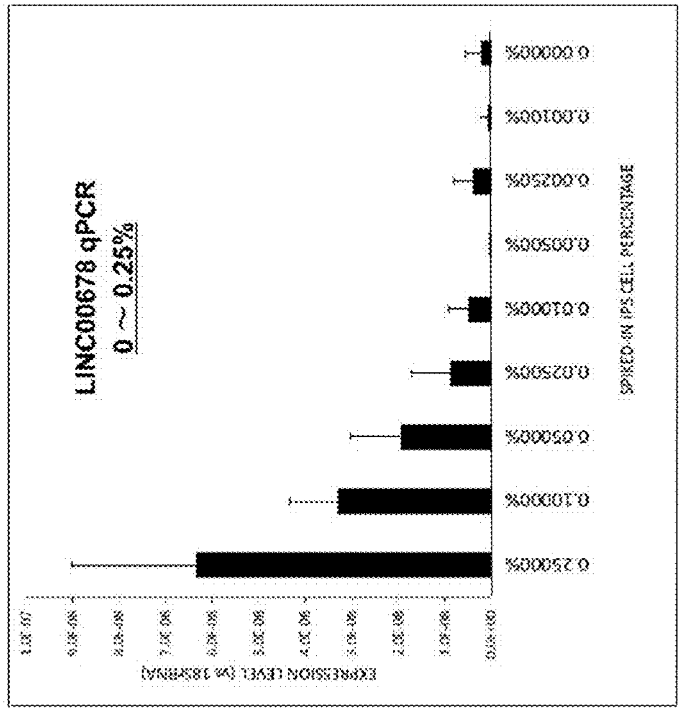

[Fig. 5]
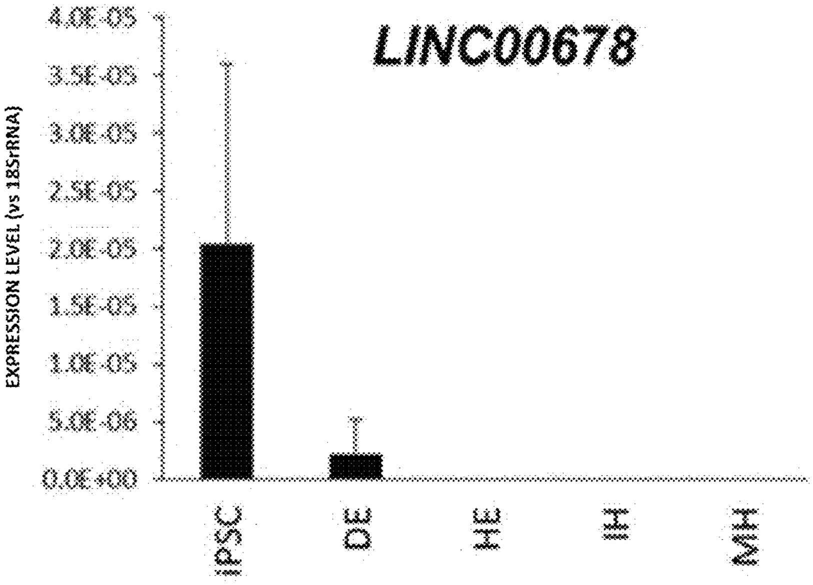

[Fig. 6]
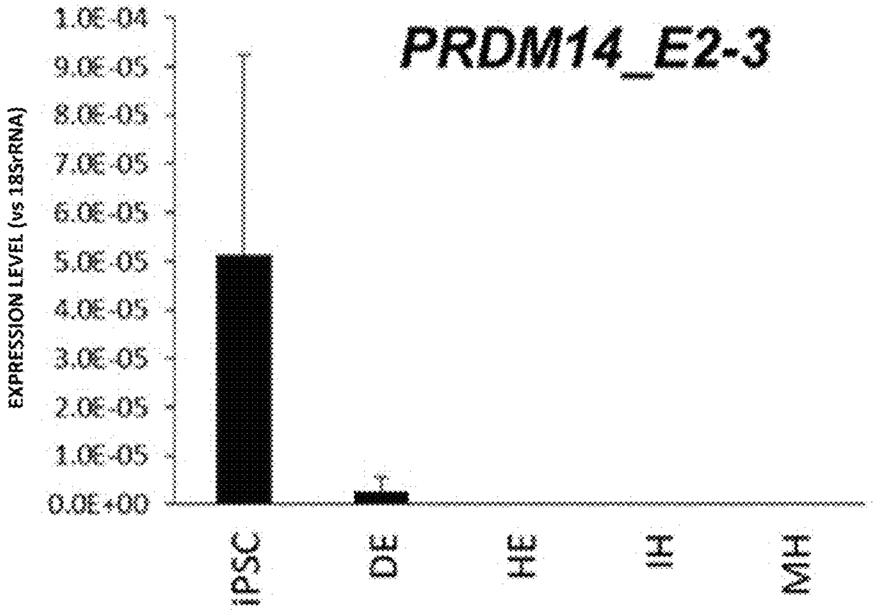

SEQUENCE LISTING

```
<160> NUMBER OF SEQ ID NOS: 53

<210> SEQ ID NO 1
<211> LENGTH: 25
<212> TYPE: DNA
<213> ORGANISM: Artificial Sequence
<220> FEATURE:
<223> OTHER INFORMATION: primer

<400> SEQUENCE: 1

catctcacca attttaaatc aggac                                    25


<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2

ctcccgtcat tctgctaaca c                                        21


<210> SEQ ID NO 3
<211> LENGTH: 18
<212> TYPE: DNA
<213> ORGANISM: Artificial Sequence
<220> FEATURE:
<223> OTHER INFORMATION: primer

<400> SEQUENCE: 3

gacgggagtg tgagatcc                                            18


<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4

acatcttctc ctgaatcctc ag                                       22


<210> SEQ ID NO 5
<211> LENGTH: 40
<212> TYPE: DNA
```

<213> ORGANISM: Artificial Sequence
<220> FEATURE:
<223> OTHER INFORMATION: primer

<400> SEQUENCE: 5
ttggaaatag ttctcggttg ctctccacat ggcgaggcac 40

<210> SEQ ID NO 6
<211> LENGTH: 43
<212> TYPE: DNA
<213> ORGANISM: Artificial Sequence
<220> FEATURE:
<223> OTHER INFORMATION: primer

<400> SEQUENCE: 6
tggtcaggtg gagtaaaaca taaggagaca cctccatgct gtc 43

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
caagaagaaa acaggttcct gg 22

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
ggttcaaagc atgaaaaaaa ttgg 24

<210> SEQ ID NO 9
<211> LENGTH: 28
<212> TYPE: DNA
<213> ORGANISM: Artificial Sequence
<220> FEATURE:
<223> OTHER INFORMATION: probe

<400> SEQUENCE: 9
ccttcacttt gagccaggca atggtcag 28

<210> SEQ ID NO 10
<211> LENGTH: 18
<212> TYPE: DNA
<213> ORGANISM: Artificial Sequence
<220> FEATURE:
<223> OTHER INFORMATION: primer

<400> SEQUENCE: 10
ccctgtcctc ctgttctt 18

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
caggagctga ttctgttgc 19

<210> SEQ ID NO 12
<211> LENGTH: 40
<212> TYPE: DNA
<213> ORGANISM: Artificial Sequence
<220> FEATURE:
<223> OTHER INFORMATION: primer

<400> SEQUENCE: 12
gttcgttggg ctggtcggct ccgtgagaaa gatccaccta 40

<210> SEQ ID NO 13
<211> LENGTH: 43
<212> TYPE: DNA
<213> ORGANISM: Artificial Sequence
<220> FEATURE:
<223> OTHER INFORMATION: primer

<400> SEQUENCE: 13
aaatcaggac ctaccagtct gcccgtctcg cagggtatca gtc 43

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
tgctcatact tgatctggat ga 22

<210> SEQ ID NO 15
<211> LENGTH: 22
<212> TYPE: DNA
<213> ORGANISM: Artificial Sequence
<220> FEATURE:
<223> OTHER INFORMATION: probe

<400> SEQUENCE: 15
aggtcctcag accgaccagc cc 22

<210> SEQ ID NO 16
<211> LENGTH: 18
<212> TYPE: DNA
<213> ORGANISM: Artificial Sequence
<220> FEATURE:
<223> OTHER INFORMATION: primer

<400> SEQUENCE: 16
ggaactctgg cccaaggt 18

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
ctgtgtgaag agaccaccaa 20

<210> SEQ ID NO 18
<211> LENGTH: 40
<212> TYPE: DNA
<213> ORGANISM: Artificial Sequence
<220> FEATURE:

<223> OTHER INFORMATION: primer

<400> SEQUENCE: 18
ttctgaggcg atcaggcagc ctccttcttg gcttactggc 40

<210> SEQ ID NO 19
<211> LENGTH: 39
<212> TYPE: DNA
<213> ORGANISM: Artificial Sequence
<220> FEATURE:
<223> OTHER INFORMATION: primer

<400> SEQUENCE: 19
gcagaccatc atggacgccg aggctttgtg tgagcaaca 39

<210> SEQ ID NO 20
<211> LENGTH: 17
<212> TYPE: DNA
<213> ORGANISM: Artificial Sequence
<220> FEATURE:
<223> OTHER INFORMATION: primer

<400> SEQUENCE: 20
gctttagccc gcctgca 17

<210> SEQ ID NO 21
<211> LENGTH: 27
<212> TYPE: DNA
<213> ORGANISM: Artificial Sequence
<220> FEATURE:
<223> OTHER INFORMATION: probe

<400> SEQUENCE: 21
gcctgcaccc aggtgaaata aacagcc 27

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
tccaaaggta tgtgaagcct 20

<210> SEQ ID NO 23
<211> LENGTH: 18
<212> TYPE: DNA
<213> ORGANISM: Artificial Sequence
<220> FEATURE:
<223> OTHER INFORMATION: primer

<400> SEQUENCE: 23
tcatctcctc acaggtgc 18

<210> SEQ ID NO 24
<211> LENGTH: 48
<212> TYPE: DNA
<213> ORGANISM: Artificial Sequence
<220> FEATURE:
<223> OTHER INFORMATION: primer

<400> SEQUENCE: 24
tctcggttga tgtaggttat ctccttgaca acgacataat ggaaacgc 48

<210> SEQ ID NO 25
<211> LENGTH: 42
<212> TYPE: DNA
<213> ORGANISM: Artificial Sequence
<220> FEATURE:
<223> OTHER INFORMATION: primer

<400> SEQUENCE: 25
tggagaccaa gagcaagacc atttgtcttt gagccacagc ac 42

<210> SEQ ID NO 26
<211> LENGTH: 22
<212> TYPE: DNA
<213> ORGANISM: Artificial Sequence
<220> FEATURE:
<223> OTHER INFORMATION: primer

<400> SEQUENCE: 26
tttacaagct gaacggtgtg tc 22

<210> SEQ ID NO 27
<211> LENGTH: 29
<212> TYPE: DNA
<213> ORGANISM: Artificial Sequence
<220> FEATURE:
<223> OTHER INFORMATION: probe

<400> SEQUENCE: 27
ggtgtgtccg aaagggacct gaagaaatc 29

<210> SEQ ID NO 28
<211> LENGTH: 22
<212> TYPE: DNA
<213> ORGANISM: Artificial Sequence
<220> FEATURE:
<223> OTHER INFORMATION: primer

<400> SEQUENCE: 28
agtggtaaga aaaattgttc ca 22

<210> SEQ ID NO 29
<211> LENGTH: 19
<212> TYPE: DNA
<213> ORGANISM: Artificial Sequence
<220> FEATURE:
<223> OTHER INFORMATION: primer

<400> SEQUENCE: 29
acagattcct tcgtgatcc 19

<210> SEQ ID NO 30
<211> LENGTH: 45
<212> TYPE: DNA
<213> ORGANISM: Artificial Sequence
<220> FEATURE:
<223> OTHER INFORMATION: primer

<400> SEQUENCE: 30
actgggtctg gtttcattat tcagtaaaaa gaccacacag tggac 45

<210> SEQ ID NO 31
<211> LENGTH: 40
<212> TYPE: DNA
<213> ORGANISM: Artificial Sequence
<220> FEATURE:
<223> OTHER INFORMATION: primer

<400> SEQUENCE: 31
caagaggact cacaagcctt cgtctagggt cgaatgtcat 40

<210> SEQ ID NO 32
<211> LENGTH: 19
<212> TYPE: DNA
<213> ORGANISM: Artificial Sequence
<220> FEATURE:
<223> OTHER INFORMATION: primer

<400> SEQUENCE: 32
cagcaggaag gggaaagca 19

<210> SEQ ID NO 33
<211> LENGTH: 22
<212> TYPE: DNA
<213> ORGANISM: Artificial Sequence
<220> FEATURE:
<223> OTHER INFORMATION: probe

<400> SEQUENCE: 33
cttccagcgc ctgggttgct cc 22

<210> SEQ ID NO 34
<211> LENGTH: 18
<212> TYPE: DNA
<213> ORGANISM: Artificial Sequence
<220> FEATURE:
<223> OTHER INFORMATION: primer

<400> SEQUENCE: 34
ccgccaggac ttttcact 18

<210> SEQ ID NO 35
<211> LENGTH: 22
<212> TYPE: DNA
<213> ORGANISM: Artificial Sequence
<220> FEATURE:
<223> OTHER INFORMATION: primer

<400> SEQUENCE: 35
agctgagaaa tgcataatcc aa 22

<210> SEQ ID NO 36
<211> LENGTH: 43
<212> TYPE: DNA
<213> ORGANISM: Artificial Sequence
<220> FEATURE:
<223> OTHER INFORMATION: primer

<400> SEQUENCE: 36
taactcagag gtcagtccct gtaggagatc agcatttgcc ctg 43

<210> SEQ ID NO 37
<211> LENGTH: 41
<212> TYPE: DNA
<213> ORGANISM: Artificial Sequence
<220> FEATURE:
<223> OTHER INFORMATION: primer

<400> SEQUENCE: 37
ccaaaggccg acctggggaa agtctctgtt cacaacactt g 41

<210> SEQ ID NO 38
<211> LENGTH: 18

<212> TYPE: DNA
<213> ORGANISM: Artificial Sequence
<220> FEATURE:
<223> OTHER INFORMATION: primer

<400> SEQUENCE: 38
ggatcgccca gtttccat 18

<210> SEQ ID NO 39
<211> LENGTH: 34
<212> TYPE: DNA
<213> ORGANISM: Artificial Sequence
<220> FEATURE:
<223> OTHER INFORMATION: probe

<400> SEQUENCE: 39
ctgattttga ggttttaata gttttcagat gctt 34

<210> SEQ ID NO 40
<211> LENGTH: 17
<212> TYPE: DNA
<213> ORGANISM: Artificial Sequence
<220> FEATURE:
<223> OTHER INFORMATION: primer

<400> SEQUENCE: 40
ttcctgtcca tgaccgc 17

<210> SEQ ID NO 41
<211> LENGTH: 17
<212> TYPE: DNA
<213> ORGANISM: Artificial Sequence
<220> FEATURE:
<223> OTHER INFORMATION: primer

<400> SEQUENCE: 41
tccttttggc cgcctct 17

<210> SEQ ID NO 42
<211> LENGTH: 41
<212> TYPE: DNA
<213> ORGANISM: Artificial Sequence
<220> FEATURE:
<223> OTHER INFORMATION: primer

<400> SEQUENCE: 42
tccggaaccc ttccatgtgc agcgaccccc cagtggatgt c 41

<210> SEQ ID NO 43
<211> LENGTH: 46
<212> TYPE: DNA
<213> ORGANISM: Artificial Sequence
<220> FEATURE:
<223> OTHER INFORMATION: primer

<400> SEQUENCE: 43
agttcacctt taagaagtca gccacactcc caatacagaa tactcc 46

<210> SEQ ID NO 44
<211> LENGTH: 19
<212> TYPE: DNA
<213> ORGANISM: Artificial Sequence
<220> FEATURE:
<223> OTHER INFORMATION: primer

<400> SEQUENCE: 44
agggtctgga atccatccg 19

<210> SEQ ID NO 45
<211> LENGTH: 24
<212> TYPE: DNA
<213> ORGANISM: Artificial Sequence
<220> FEATURE:
<223> OTHER INFORMATION: probe

<400> SEQUENCE: 45
ggaatccatc cgtgtcaccg gacc 24

<210> SEQ ID NO 46
<211> LENGTH: 17
<212> TYPE: DNA
<213> ORGANISM: Artificial Sequence
<220> FEATURE:
<223> OTHER INFORMATION: primer

<400> SEQUENCE: 46
tcggttccag ttcacgg 17

<210> SEQ ID NO 47
<211> LENGTH: 19
<212> TYPE: DNA
<213> ORGANISM: Artificial Sequence
<220> FEATURE:
<223> OTHER INFORMATION: primer

<400> SEQUENCE: 47
gacttcacca aacaccgtc 19

<210> SEQ ID NO 48
<211> LENGTH: 38
<212> TYPE: DNA
<213> ORGANISM: Artificial Sequence
<220> FEATURE:
<223> OTHER INFORMATION: primer

<400> SEQUENCE: 48
atggtgcagg ctggctgggg gaggacctgc acttcgtt 38

<210> SEQ ID NO 49
<211> LENGTH: 41
<212> TYPE: DNA
<213> ORGANISM: Artificial Sequence
<220> FEATURE:
<223> OTHER INFORMATION: primer

<400> SEQUENCE: 49
tccccccaga cagctctggc atagaccttc tggaagttga a 41

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
tgctccaggc tgggagtgac 20

<210> SEQ ID NO 51
<211> LENGTH: 25
<212> TYPE: DNA
<213> ORGANISM: Artificial Sequence -continued

```
<220> FEATURE:
<223> OTHER INFORMATION: primer

<400> SEQUENCE: 51

atctgattct cttcctcaaa ctctg                                             25


<210> SEQ ID NO 52
<211> LENGTH: 32
<212> TYPE: DNA
<213> ORGANISM: Artificial Sequence
<220> FEATURE:
<223> OTHER INFORMATION: probe

<400> SEQUENCE: 52

ttctcttcct caaactctgg ataaagactc cc                                     32


<210> SEQ ID NO 53
<211> LENGTH: 42
<212> TYPE: DNA
<213> ORGANISM: Artificial Sequence
<220> FEATURE:
<223> OTHER INFORMATION: template

<400> SEQUENCE: 53

tgggtgggga aggaggaaca atagtatagc ttccagaaga ga                          42
```

SENSITIVE DETECTION METHOD FOR UNDIFFERENTIATED MARKER GENES

SEQUENCE LISTING SUBMISSION VIA EFS-WEB

A computer readable text file, entitled "SequenceListing.txt" created on Jun. 15, 2022, with a file size of 9,829 bytes and contains the sequence listing for this application and is hereby incorporated by reference in its entirety.

TECHNICAL FIELD

The present invention relates to a method for detecting undifferentiation marker genes with high sensitivity.

BACKGROUND ART

Technical requirements for ensuring the quality and safety of products processed from human cells among regenerative medical products are stipulated in a plurality of guidelines (Non-Patent Document No. 1). Transplantation and administration of the final products to humans pose a risk of tumorigenesis due to residual undifferentiated pluripotent stem cells, since such products are processed from human pluripotent stem cells having tumorigenicity as in the case of products processed from human embryonic stem cells (human ES cells) and products processed from human induced pluripotent stem cells (human iPS cells).

In order to prevent the contamination with undifferentiated pluripotent stem cells (hereinafter referred to as undifferentiated cells), it is required to increase the abundance rate of cells of interest by improving the differentiation efficiency (setting differentiation conditions such as medium components, cytokines and growth factors) and to eliminate the contaminating undifferentiated cells through enrichment purification steps (e.g., selective separation using antibodies or lectins) as necessary. At the same time, for the practical application of therapeutic means for transplanting administering a regenerative medical product, to humans, a test method for confirming the removal and remaining of undifferentiated cells is indispensable, and the ability to detect undifferentiated cells with the highest possible sensitivity is strongly required.

For the detection of residual undifferentiated cells in the intermediate products and/or final products of regenerative medical products, evaluation by an in vitro test of detecting specific molecular markers is effective. Examples of the method include not only a flow cytometry method utilizing the presence or absence of a specific antigen on the cell surface and a method for detecting molecular markers (e.g., podocalyxin, laminin and CD30, Non-Patent Document Nos. 2, 3 and 4) in the culture supernatants, but also quantitative Reverse Transcription-Polymerase Chain Reaction, hereinafter qRT-PCR method, (Non-Patent Document No. 5) that targets genes confirmed to exhibit high-level expression in undifferentiated cells and a digital PCR method (Non-Patent Document No. 6). The polymerase chain reaction (PCR method), which is the basis of the qRT-PCR method and the digital PCR method, is theoretically capable of exponentially amplifying a target DNA level by repeating 25 to 40 times the three-step temperature changes: 1) thermal denaturation (94° C. to 98° C., 30 seconds, etc.)→2) primer annealing (50° C. to 65° C., 30 seconds, etc.)→3) extension reaction (68° C. to 72° C., 60 seconds, etc.). The amount of products amplified by the PCR method can also be quantitatively analyzed using probes labeled with fluorescent dyes etc., since the amount of PCR products correlates both with the amount of a template nucleic acid in a sample and the number of reaction cycles. Hence, the PCR method is recognized as a standard technique for gene amplification and specifically as a method capable of amplifying a small amount of a template nucleic acid in a relatively short period of time.

However, even if the qRT-PCR method, which is known as a sensitive method, is used for the detection of undifferentiation marker genes, the quantification and/or determination accuracy is not sufficient. This is because the number of the molecules of a target undifferentiation marker gene in the intermediate product and/or final product of a regenerative medical product, is so small that the amplification efficiency of the target molecule decrease, and that exponential amplification is hindered. In such a case, it is possible to ensure amplification efficiency by increasing the quantity of nucleic acids per reaction to increase the number of target molecules, but in the case of the qRT-PCR method with a typical liquid volume, the upper limit should be about 100 ng per reaction. This is because the amplification reaction is inhibited and non-specific amplification occurs as the amount of contaminating nucleic acids increases: In order to increase the quantity of nucleic acids beyond this upper limit, it is necessary to increase the reaction solution volume per reaction. However, the general PCR reaction is not preferable since in order to perform the above-mentioned three-step temperature changes quickly and accurately, the reaction solution volume is limited to about 5 μL to 100 μL at which the reaction tube fits in the thermal block on the thermal cycler as a dedicated device.

PCR is a reaction that has conventionally been performed in a single container, but digital PCR involves distributing a nucleic acid sample into microcompartments (oil droplets, etc.) to perform limiting dilution, followed by a nucleic acid amplification reaction, and is attracting attention as a method for quantifying the number of molecules of a target nucleic acid using a statistical technique. However, digital PCR has disadvantages such as the need for a special and expensive dedicated device and the high test cost, and thus has not been widely used.

Further, in facilities for handling multiple types of cells and cells derived from multiple individuals (cell donors), the presence or absence of cell contamination is analyzed by SNPs (single nucleotide polymorphism) analysis, but contamination of cells of the same individual, for example, cross-contamination of undifferentiated cells into differentiated cells cannot be detected by SNPs analysis.

In numerous attempts to improve the PCR method, which is a standard nucleic acid amplification method, an isothermal nucleic acid amplification method has been developed, in which an amplification reaction is rapidly carried out under mild temperature conditions and by which a nucleic acid is amplified with high efficiency. As methods capable of amplifying nucleic acids under constant temperature conditions, multiple methods have been reported and they include, for example, a LAMP method (Loop-mediated Isothermal Amplification, Patent Document No. 1), a NASBA method (Nucleic Acid Sequence-. Based Amplification, Patent Document Nos. 2 and 3), an SDA method (Strand Displacement Amplification, Patent Document No. 4), a TRC method (Transcription Reverse-transcription Concerted reaction, Patent Document No. 5), and an ICAN method (Isothermal and Chimeric primer-initiated Amplification of Nucleic acids, Patent Document No. 6). The respective methods have their own features, such as the one requiring multiple enzymes, the one limited in the types of template nucleic acids, and the one requiring special primers such as chimeric primers, so an optimum method should be selected according to the purpose.

All of these methods have an advantage of not requiring strict temperature control unlike the PCR method, because an amplification reaction in these methods proceeds continuously at a constant temperature (40° C. to 70° C.). However, at the present time, there is no report that a method for detecting an undifferentiation marker gene with high sensitivity has been established by taking advantage of the isothermal nucleic acid amplification method.

PRIOR ART LITERATURE

Non-Patent Documents

Non-Patent Document No. 1:
Considerations in studies to detect undifferentiated pluripotent stem cells and transformed cells, tumorigenicity and genetic instability of human cell-based products (the MHLW, PSEHB/ELD Notification No. 0627-1, Jun. 27, 2019)
Non-Patent Document No. 2:
Tateno H et al. A medium hyperglycosylated podocalyxin enables noninvasive and quantitative detection of tumorigenic human pluripotent stem cells. Sci Rep. 2014; 4:4069.
Non-Patent Document No. 3:
Tano K et al. A novel in vitro method for detecting undifferentiated human pluripotent stem cells as impurities in cell therapy products using a highly efficient culture system. PLOS One. 2014; 9: e110496.
Non-Patent Document No. 4:
Immunologic targeting of CD30 eliminates tumorigenic human pluripotent stem cells, allowing safer clinical application of hipSC-based cell therapy. Sci Rep. 2018 Feb. 27; 8 (1): 3726.
Non-Patent Document No. 5:
Kuroda T et al. Highly sensitive in vitro methods for detection of residual undifferentiated cells in retinal pigment epithelial cells derived from human iPS cells. Plos One. 2012; 7: e37342.
Non-Patent Document No. 6:
Kuroda, T et al. Highly sensitive droplet digital PCR method for detection of residual undifferentiated cells in cardiomyocytes derived from human pluripotent stem cells. Regen Therapy 2015; 2:17-23.
Non-Patent Document No. 7:
Lin, Y et al. Genome dynamics of the human embryonic kidney 293 lineage in response to cell biology manipulations. Nat Commun 2014; 5:4767.
Non-Patent Document No. 8:
Sekine, K et al. Robust detection of undifferentiated iPSC among differentiated cells. Sci Rep 2020; 10:10293.

Patent Document's

Patent Document No. 1: Japanese Patent No. 3313358
Patent Document No. 2: Japanese Patent No. 2650159
Patent Document No. 3: Japanese Patent No. 3152927
Patent Document No. 4: U.S. Pat. No. 5,270,184
Patent Document No. 5: Japanese Patent No. 4438110
Patent Document No. 6: Japanese Patent No. 3433929

DISCLOSURE OF THE INVENTION

Problem for Solution by the Invention

The present invention has been made in a view of the above current situation, and an object of the present invention is to provide a method for simply detecting residual undifferentiated cells in the intermediate products and/or final products of regenerative medical products, with high sensitivity using an isothermal nucleic acid amplification method, particularly the LAMP method, and a kit therefor.

Means to Solve the Problem

The present inventors have focused on the fact that in the PCR method, in which dissociation and polymerization are repeated with changes in reaction temperature, [1] the reaction solution volume is limited in order to control changes in reaction temperature quickly and accurately, and the quantity of a nucleic acid sample cannot be increased, and [2] when a large amount of nucleic acids other than target nucleic acids is brought in, non-specific nucleic acid amplification may occur, or nucleic acid amplification and detection may be inhibited. The present inventors have considered that through the use of an isothermal nucleic acid amplification method capable of nucleic acid amplification with high specificity and high amplification efficiency under constant temperature conditions, the reaction solution volume can be increased and undifferentiation marker genes can be specifically detected even when a large amount of nucleic acids other than target nucleic acids is brought in. As a result of intensive studies, the present inventors have established a sensitive and simple detection method for detecting residual undifferentiated cells in the intermediate products and/or final products of regenerative medical products, through detection of undifferentiation marker genes that are expressed at high levels in undifferentiated cells by the LAMP method. Moreover, as a result of examining the applicability to a plurality of undifferentiation marker genes, the present inventors have confirmed that this detection method is versatile and thus have completed the present invention.

Specifically, the present invention is summarized as follows.

(1) A method for detecting presence, absence, or amount of undifferentiated cells in a non-undifferentiated cell population, wherein RNA derived from an undifferentiation marker gene exhibiting a significant difference in expression level between the undifferentiated cells and the non-undifferentiated cells in a sample containing a nucleic acid derived from the cell population of interest is detected by an isothermal nucleic acid amplification method.

(2) The method according to (1), wherein the differentiation state of the cell population of interest at the time of and/or after directed differentiation from the undifferentiated cells to the non-undifferentiated cells is evaluated.

(3) The method according to (2), wherein the undifferentiated cells are pluripotent stem cells or somatic stem cells.

(4) The method according to any one of (1) to (3), wherein the RNA to be detected is present in the sample in an amount equal to or higher than the limit of detection of the isothermal nucleic acid amplification method and is present in the non-undifferentiated cells in an amount equal to or below the limit of detection of the isothermal nucleic acid amplification method and wherein when the RNA to be detected is detected in the sample, the result is determined to be positive, and when the RNA to be detected is not detected in the sample, the result is determined to be negative.

(5) The method according to any one of (1) to (4), wherein the RNA derived from an undifferentiation marker gene satisfies:

(i) the ratio of the RNA expression level in the undifferentiated cells to the RNA expression level in the non-undifferentiated cells is $10^4$ or more times, and/or (ii) the RNA expression level in the non-undifferentiated cells is $1\times10^4$ copies or less per μg of the total RNA level.

(6) The method according to any one of (1) to (5), wherein a nucleic acid synthesized from the RNA to be detected serving as a template is amplified isothermally using at least four different primers specifically designed to recognize six distinct regions on the target sequence.

(7) The method according to any one of (1) to (6), wherein the nucleic acid is amplified by DNA polymerase having strand displacement activity.

(8) The method according to (7), wherein the nucleic acid synthesized by reverse transcriptase from the RNA to be detected serving as a template is amplified isothermally with DNA polymerase having strand displacement activity using at least four different primers specifically designed to recognize six distinct regions on the target sequence.

(9) The method according to any one of (6) to (8), wherein the nucleic acid amplification is performed using one or more additional primers for further accelerating the reaction.

(10) The method according to (9), wherein the nucleic acid synthesized by reverse transcriptase from the RNA to be detected serving as a template is amplified isothermally with DNA polymerase having strand displacement activity using at least four different primers specifically designed to recognize six distinct regions on the target sequence, as well as one or more additional primers for further accelerating the reaction.

(11) The method according to any one of (1) to (10), wherein the reverse transcription of the RNA to be detected to the amplification and the detection of RNA are consecutively performed.

(12) A kit for detecting presence, absence, or amount of undifferentiated cells in a non-undifferentiated cell population, comprising a reagent with which RNA derived from an undifferentiation marker gene exhibiting a significant difference in expression level between the undifferentiated cells and the non-undifferentiated cells is detected by an isothermal nucleic acid amplification method.

(13) The kit according to (12), wherein the reagent comprises a primer.

(14) The kit according to (13), wherein the reagent further comprises a probe and/or a colorimetric reagent.

Effect of the Invention

The present invention as summarized above enables sensitive detection of undifferentiation marker genes using an isothermal nucleic acid amplification method, particularly the LAMP method, whereby the accuracy of a test for determining the presence or absence of undifferentiated cells in the intermediate products and/or final products of regenerative medical products can be improved. Furthermore, the present invention utilizes an amplification reaction that is not easily affected by contaminants, and thus a nucleic acid sample can be prepared by a simple method.

The present specification encompasses the contents disclosed in the specification and/or drawings of Japanese Patent Application No. 2019-207004 based on which the present patent application claims priority.

BRIEF DESCRIPTION OF THE DRAWINGS

FIG. 1 The primer design of the RT-LAMP method is shown.

FIG. 2 The amplification principle of the RT-LAMP method is shown.

FIG. 3 The design of loop primers is shown.

FIG. 4 The results of examining the detection sensitivity for undifferentiation marker genes in undifferentiated iPS cell spike-in experiments are shown. By mixing undifferentiated iPS cells into hepatic endoderm cells and making comparison with a group into which undifferentiated iPS cells had not been mixed, the detection sensitivity was examined by qRT-PCR. FIG. 4(*a*) shows the expression level (vs. 18S rRNA) at a spiked-in iPS cell percentage of 0 to 5%. FIG. 4(*b*) shows enlarged the result for the spiked-in iPS cell percentage of 0 to 0.25% in FIG. 4(*a*).

FIG. 5 The expression level (vs. 18S rRNA) of an undifferentiation marker gene (LINC00678) at each differentiation stage of directed differentiation from human iPSC to hepatocytes is shown. "DE" is Definitive Endoderm, "HE" is Hepatic Endoderm, "IH" is Immature Hepatocyte-like cell, and "MH" is Mature Hepatocyte-like cell.

FIG. 6 The expression level (vs. 18S rRNA) of an undifferentiation marker gene (PRDM14) at each differentiation stage of directed differentiation from human iPSC to hepatocytes is shown. "DE" is Definitive Endoderm, "HE" is Hepatic Endoderm, "IH" is Immature Hepatocyte-like cell, and "MH" is Mature Hepatocyte-like cell.

BEST MODES FOR CARRYING OUT THE INVENTION

Hereinbelow, the present invention will be described in detail.

The present invention provides a method for detecting presence, absence, or amount of undifferentiated cells in a non-undifferentiated cell population, wherein RNA derived from an undifferentiation marker gene exhibiting a significant difference in expression level (amount present) between the undifferentiated cells and the non-undifferentiated cells in a sample containing a nucleic acid derived from the cell population of interest is detected by an isothermal nucleic acid amplification method.

In the present invention, undifferentiated cells are preferably human or non-human mammalian cells having pluripotency. For example, undifferentiated cells are at least one type of pluripotent stem cells selected from the group consisting of embryonic carcinoma cells (EC cells), embryonic stem cells (ES cells), induced pluripotent stem cells (iPS cells), embryonic germ cells (EG cells), somatic (tissue) stem cells, and the like.

In the present invention, non-undifferentiated cells may be any cell's that can be distinguished from undifferentiated cells. Examples of the non-undifferentiated cells can include cells that are derived from pluripotent stem cells and which do not remain in the initial state as undifferentiated cells but are "well-differentiated cells" and "cells in the process of differentiation" into cells of interest (e.g., hepatocytes, vascular endothelial cells, nerve cells, etc.) The degree of differentiation of "cells in the process of differentiation" is not critical and the non-undifferentiated cells may be cells differentiated to such an extent that they are destined to differentiate into cells of interest, or they may be differentiated to such an extent that they are yet to be destined to differentiate into cells of interest. The non-undifferentiated cells may be "cells constituting a cell population in various states such as cells that are fully differentiated and cells that are still in the process of differentiation, on the way to differentiation into cells of interest (e.g., hepatocytes, vascular endothelial cells, and nerve cells)". The non-undifferentiated cells may also be "cultured cells not limited to differentiated cells derived from pluripotent stem cells".

In the present invention, the term "sample" means a "sample containing a nucleic acid derived from a cell population of interest", and examples of the sample can include "a nucleic acid extracted from a cell population", "a cell population not undergoing a nucleic acid extraction process", "a culture solution containing a cell population, not undergoing a nucleic acid extraction", and "a culture solution containing no cell population, not undergoing a nucleic acid extraction". The "cell population of interest" may be a non-undifferentiated cell population that may contain undifferentiated cells.

In the method of the present invention, RNA derived from an undifferentiation marker gene exhibiting a significant difference in expression level between undifferentiated cells and non-undifferentiated cells is detected by an isothermal nucleic acid amplification method. Such RNA derived from an undifferentiation marker gene exhibiting a significant difference in expression level between undifferentiated cells and non-undifferentiated cells may be any RNA that has a significant difference in expression level between undifferentiated cells and non-undifferentiated cells, and is preferably RNA showing a decrease in expression level with the passage of time as the differentiation process proceeds. For example, on the basis of the quantitative analysis data obtained by qRT-PCR, the presence or absence of a significant difference can be identified by determining a p value of less than 0.05 as the presence of a significant difference when the significance level is set to 5% in the Student's t test.

In the method of the present invention for detecting the presence on absence of undifferentiated cells in a non-undifferentiated cell population, it is desirable to detect RNA whose expression level is decreased in the differentiation process, and further, the decrease in expression level is desirably a remarkable one. In a test for the purpose of denying the contamination with undifferentiated cells, which requires sensitive detection performance, the higher the expression level of RNA to be detected in undifferentiated cells, the better, and what is more, the lower the RNA expression level in non-undifferentiated cells, the better. Specifically: the ratio of the expression level of an RNA in undifferentiated cells to the RNA expression level in non-undifferentiated cells is desirably $10^4$ times or more, more desirably $10^5$ times or more, and most desirably $10^6$ times or more; and/or the RNA expression level in non-undifferentiated cells is desirably $1\times10^4$ copies or less per μg of total RNA level, more desirably $1\times10^3$ copies or less, even more desirably $1\times10^2$ copies or less, further desirably $1\times10$ copies or less, and ideally the number of copies is close to zero. Specific examples of RNA that can be used in the present invention include, but are not limited to, LINC00678, SFRP2, PRDM14, USP44, ESRG, CNMD, LIN28A, SOX2, OCT4, NANOG, TDGF1, and TNFRSF8, as well as known genes disclosed in papers etc. to exhibit high expression levels in undifferentiated cells but low expression levels in non-undifferentiated cells, as determined by transcriptome analysis and by a quantitative PCR method.

Note that RNA may be RNA transcribed from genomic DNA (in the case of eukaryotes, genomic DNA possessed by organelles such as the mitochondrial genome is also included herein), which may be further modified or processed RNA after transcription, as exemplified by microRNA or circular RNA. Furthermore, such RNA may be RNA not encoding a protein, or may be a partial decomposition product of RNA containing a target sequence for nucleic acid amplification. The genome may be any one of the following: a region encoding a protein, a region encoding a transcriptional regulatory region such as a promoter or an enhancer, and a non-coding region other than these regions.

A difference in the RNA expression level of an undifferentiation marker gene between non-undifferentiated cells and undifferentiated cells, which is specifically described in the above section, can be described by the following calculation conditions (simulation).

Factors that determine the method by which undifferentiated cells present in trace amounts can be detected with high sensitivity are [1] the quantity of nucleic acids per reaction, [2] the RNA expression level of an undifferentiation marker gene, [3] the percentage of undifferentiated cells.

[1] In the quantity of nucleic acids per reaction, the culture status of a non-undifferentiated cell population as a test sample and the number of cells collected, the extraction rate of a nucleic acid sample in the extraction operation after cell collection, and the degree of purification and the concentration rate are involved. On the other hand, it is known that there is a certain limit on the quantity of nucleic acids per reaction in the gene amplification reaction. In the PCR method well known for gene amplification reactions in genetic testing, a great excess quantity of nucleic acids is known to inhibit the PCR reaction and interfere with the detection of target products. Factors responsible for this include a decrease in the function of polymerase due to the depletion of magnesium ions that contribute to the structural stabilization of nucleic acid, and a delay in the single-strand formation of a nucleic acid sample due to heat denaturation. Therefore, in PCR, in the case of human genomic DNA, a maximum of 500 ng (0.5 μg) per reaction is set as a guide for the upper limit of the quantity per reaction. In addition, in the case of the qRT-PCR method with a typical liquid volume intended for quantification, the upper limit is about 100 ng per reaction. For this reason, in the PCR reaction, the quantity of nucleic acids per reaction is limited to a small value, so it is difficult to further increase the limit of detection (LOD) of the percentage of undifferentiated cells. As a feature of the method of the present invention, it is required that nucleic acid samples derived from a cell population that may contain undifferentiated cells be subjected to a single genetic test in the largest possible amounts. Hence, a test method that is not inhibited or is not easily inhibited by a great excess quantity of nucleic acid samples is desired.

[2] Regarding the expression level of an undifferentiation marker gene, RNA is desirably derived from a gene whose RNA expression level significantly changes in the process of the formation and specialization (differentiation) of cells, tissues, organs, and individuals from the state of undifferentiated cells. Specifically, RNA desired herein shows a decrease in expression level in the process of differentiation, with the decrease in its expression level being a remarkable change (high expression level in undifferentiated cells and low expression level in differentiated cells).

In the case of a gene having such a property that the RNA expression level remains unchanged or hardly changes in the differentiation process of non-undifferentiated cells as a test sample, the progress of the differentiation process or the percentage of undifferentiated cells cannot be confirmed even by a measurement system capable of quantifying the RNA expression level.

Further, if a gene expresses at no or trace RNA level in cells in an undifferentiated state, such a gene is not suitable as a marker in a test for denying the contamination with the slightest amount of undifferentiated cells having tumorigenicity.

As described above, requirements for the marker gene in the present invention are a high RNA expression level in undifferentiated cells and a low RNA expression level in differentiated cells. Moreover, it is further desired that a decrease in RNA expression level in the differentiation process is remarkable.

[3] The model case is shown below with specific figures in the range of undifferentiated cell percentage from 0.1% ($1\times10^{-3}$) to 0%.

As an example, the RNA expression levels of a marker gene in undifferentiated cells and in the process of differentiation into non-undifferentiated cells are set as shown in the following conditions.

Very high:
- $1\times10^{7}$ copies or more/1 μg (total RNA) ($1\times10^{2}$ copies or more/10 μg total RNA)
- $3\times10^{6}$ copies or more/1 μg (total RNA) (3×10 copies or more/10 μg total RNA)
- $1\times10^{6}$ copies or more/1 μg (total RNA) (1×10 copies or more/10 μg total RNA)

High:
- $3\times10^{5}$ copies or more/1 μg (total RNA) (3 copies or more/10 μg total RNA)
- $1\times10^{5}$ copies of more/1 μg (total RNA) (1 copies or more/10 μg total RNA)

Slightly low:
- $3\times10^{4}$ copies or more/1 μg (total RNA)
- $1\times10^{4}$ copies or more/1 μg (total RNA)
- $3\times10^{3}$ copies or more/1 μg (total RNA)

Low:
- $1\times10^{3}$ copies or less/1 μg (total RNA)
- $3\times10^{2}$ copies or less/1 μg (total RNA)
- $1\times10^{2}$ copies or less/1 μg (total RNA)

Very low:
- 3×10 copies or less/1 μg (total RNA)
- 1×10 copies or less/1 μg (total RNA)
- 0 copy/1 μg (total RNA)

The percentage of undifferentiated cells in a non-undifferentiated cell population during the differentiation process is in the range of 0.1% ($1\times10^{-3}$) to 0.00005% ($5\times10^{-7}$), and the RNA expression level of a marker gene per 10 μg of total RNA is calculated assuming 6 patterns as follows:

1) When a marker gene is expressed to a very high level in undifferentiated cells, but is expressed at a very low (close to zero) level in non-undifferentiated cells of interest: (the ratio of the expression level before differentiation to the expression level after differentiation ranges from $10^{6}$ to $10^{7}$ or more)
2) When a marker gene is expressed to a high level in undifferentiated cells, but is expressed at a very low (close to zero) level in non-undifferentiated cells of interest: (the ratio of the expression level before differentiation to the expression level after differentiation ranges from $10^{5}$ to $10^{6}$)
3) When a marker gene is expressed to a slightly low level in undifferentiated cells, and is expressed at a very low (close to zero) level in non-undifferentiated cells of interest: (the ratio of the expression level before differentiation to the expression level after differentiation ranges from $10^{4}$ to $10^{5}$)
4) When a marker gene is expressed to a very high level in undifferentiated cells, but is expressed at a low level in non-undifferentiated cells of interest: (the ratio of the expression level before differentiation to the expression level after differentiation ranges from $10^{4}$ to $10^{5}$)
5) When a marker gene is expressed to a high level in undifferentiated cells, but is expressed at a low level in non-undifferentiated cells of interest: (the ratio of the expression level before differentiation to the expression level after differentiation ranges from $10^{2}$ to $10^{3}$)
6) When a marker gene is expressed to a slightly low level in undifferentiated cells and is expressed at a low level in non-undifferentiated cells of interest: (the ratio of the expression level before differentiation to the expression level after differentiation ranges from 10 to $10^{2}$)

Note that the test method based on the gene amplification method represented by PCR is a method that involves specifically amplifying a target sequence contained in a test sample and detecting the same after amplification or simultaneously with amplification; the detection sensitivity of this method is represented by the number of target sequence copies per reaction. Theoretically, an amplification reaction proceeds from one copy/test, and the test method is known as one that exhibits high sensitivity and high specificity. This property is shared by the LAMP method, which is one of the gene amplification methods. Clinical diagnostic test reagents (commercially available products) for the LAMP method are characterized by a minimum detection sensitivity of 10 copies/test (e.g., Loopamp SARS coronavirus detection reagent kit). In this way, in infectious disease tests that involve amplifying and detecting specific nucleotide sequences derived from pathogenic microorganisms, sensitive detection performance at the level of several copies/test is required. However, by varying the conditions for the reaction composition including the nucleotide sequences of primers to be used, the amount of primers, and the concentrations of substrates, enzymes and catalysts therefor, the detection sensitivity can also be adjusted from 10 copies/test to several thousand copies/test. In other words, the detection sensitivity of the tests is variable depending on the various conditions involved in the reaction. In particular, in the method of the present invention, it is possible to provide a method of adjusting the detection sensitivity via a reaction substrate (e.g., dNTPs).

The concentration of a reaction substrate (dNTPs) to be used in the present invention is not particularly limited, and may be, for example, 0.25 mM to 3.0 mM, 0.5 mM to 2.5 mM, or 1 mM to 2 mM, and can be varied depending on the combination with other conditions for the reaction composition, including the nucleotide sequences of primers to be used, the amount of primers, as well as enzymes and catalysts therefor. For example, in a reaction composition including a small number of template nucleic acid copies (e.g., 10 copies per test) and with the concentration of reaction substrates (dNTPs) being used as a sole variable parameter (for example, 0.5 mM to 2.5 mM), the presence or absence of amplification reaction and reaction rate are tested within a certain period of time (e.g., 90 minutes) after the start of the test. In this case, it can be said that the earlier the start of the amplification reaction (for example, within 20 minutes), the more optimum or the closer to the optimum the concentration of the substrates. Based on such tests, the optimum concentration of sensitively detectable substrates (dNTPs) can be determined.

Therefore, the concentration of the reaction substrates (dNTPs) to be used in the present invention may be within ±50% of the optimum concentration (for example, 0.5 mM to 1.5 mM in the case where the optimum concentration is 1.0 mM), and preferably within ±30% (for example, 0.7 mM to 1.3 mM in the case where the optimum concentration is 1.0 mM), and the detection sensitivity can be adjusted depending on the concentration of the reaction substrates.

In the table of the expression level combination patterns in the following differentiation process, the number of RNA expression copies of an undifferentiation marker gene contained in 10 μg of total RNA per reaction is shown in each matrix. Regarding this method in which the detection sensitivity is adjustable, when the minimum detection sensitivity of 1) to 3) is set to 10 copies/test and that of 4) to 6) is set to $4\times10^3$ copies/test, positive cells are highlighted.

1) When a marker gene is expressed to a very high level in undifferentiated cells but is expressed at a very low (close to zero) level in non-undifferentiated cells of interest: (the ratio of the expression level before differentiation to the expression level after differentiation ranges from $10^6$ to $10^7$ or more)

| RNA expression level (copies/μg) per 1 μg of total RNA extracted from cell | | | Percentage of undifferentiated cells | | | | | | | | |
|---|---|---|---|---|---|---|---|---|---|---|---|
| population in differentiation process | | Differentiation process | 0.1% $1\times10^{-3}$ | 0.01% $1\times10^{-4}$ | 0.005% $5\times10^{-5}$ | 0.001% $1\times10^{-5}$ | 0.0005% $5\times10^{-6}$ | 0.0001% $1\times10^{-6}$ | 0.00005% $5\times10^{-7}$ | | 0.00000% |
| $1\times10^7$ | Very high | Undifferentiated | ≒1 × $10^5$ | ≒1 × $10^4$ | ≒5 × $10^3$ | ≒1 × $10^3$ | ≒5 × $10^2$ | ≒1 × $10^2$ | ≒5 × 10 | . . . | ≒0 |
| $3\times10^6$ | | ↓ | ≒3 × $10^4$ | ≒3 × $10^3$ | ≒2 × $10^3$ | ≒3 × $10^2$ | ≒2 × $10^2$ | ≒3 × 10 | ≒2 × 10 | | ≒0 |
| $1\times10^6$ | | | ≒1 × $10^4$ | ≒1 × $10^3$ | ≒5 × $10^2$ | ≒1 × $10^2$ | ≒5 × 10 | ≒1 × 10 | ≒5 | | ≒0 |
| $3\times10^5$ | High | | ≒3 × $10^3$ | ≒3 × $10^2$ | ≒2 × $10^2$ | ≒3 × 10 | ≒2 × 10 | ≒3 | ≒2 | | ≒0 |
| $1\times10^5$ | | | ≒1 × $10^3$ | ≒1 × $10^2$ | ≒5 × 10 | ≒1 × 10 | ≒5 | ≒1 | ≒0 | | ≒0 |
| $3\times10^4$ | Slightly | | ≒3 × $10^2$ | ≒3 × 10 | ≒2 × 10 | ≒3 | ≒2 | ≒0 | ≒0 | | ≒0 |
| $1\times10^4$ | low | | ≒1 × $10^2$ | ≒1 × 10 | ≒5 | ≒1 | ≒0 | ≒0 | ≒0 | | ≒0 |
| $3\times10^3$ | | | ≒3 × 10 | ≒3 | ≒2 | ≒0 | ≒0 | ≒0 | ≒0 | | ≒0 |
| $1\times10^3$ | Low | | ≒1 × 10 | ≒1 | ≒0 | ≒0 | ≒0 | ≒0 | ≒0 | | ≒0 |
| $3\times10^2$ | | | ≒3 | ≒0 | ≒0 | ≒0 | ≒0 | ≒0 | ≒0 | | ≒0 |
| $1\times10^2$ | Very low | | ≒1 | ≒0 | ≒0 | ≒0 | ≒0 | ≒0 | ≒0 | | ≒0 |
| 3 × 10 | | | ≒0 | ≒0 | ≒0 | ≒0 | ≒0 | ≒0 | ≒0 | | ≒0 |
| 1 × 10 | | Non- | ≒0 | ≒0 | ≒0 | ≒0 | ≒0 | ≒0 | ≒0 | | ≒0 |
| 0 | | undifferentiated | ≒0 | ≒0 | ≒0 | ≒0 | ≒0 | ≒0 | ≒0 | | ≒0 |

When the minimum detection sensitivity of the LAMP reaction (10 μg of total RNA is subjected to the reaction) is set to 10 copies per reaction, the limit of detection (LOD) of the percentage of undifferentiated cells is 0.00005% (5×$10^{-7}$). Even if the quantity of total RNA per test is reduced to one tenth (1 μg), the percentage of undifferentiated cells can be detected up to 0.0001% (1×$10^{-6}$).

2) When the RNA expression level in non-undifferentiated cells is very low, if not zero, the minimum detection sensitivity of the LAMP reaction may be adjusted (adjusted, for example, in such a manner that the result is positive with 50 to 100 copies) without significantly impairing the limit of detection (LOD) of the percentage of undifferentiated cells. When a marker gene is expressed to a high level in undifferentiated cells, but is expressed at a very low (close to zero) level in non-undifferentiated cells of interest: (the ratio of the expression level before differentiation to the expression level after differentiation ranges from $10^5$ to $10^6$)

| RNA expression level (copies/μg) per 1 μg of total RNA extracted from cell population in differentiation process | | Differentiation process | Percentage of undifferentiated cells 0.1% 1 × $10^{-3}$ | 0.01% 1 × $10^{-4}$ | 0.005% 5 × $10^{-5}$ | 0.001% 1 × $10^{-5}$ | 5 × $10^{-6}$ 0.0005% | 1 × $10^{-6}$ 0.0001% | 5 × $10^{-7}$ 0.00005% | | 0.00000% |
|---|---|---|---|---|---|---|---|---|---|---|---|
| 3 × $10^5$ | High | Undifferentiated | ≒3 × $10^3$ | ≒3 × $10^2$ | ≒2 × $10^2$ | ≒3 × 10 | ≒2 × 10 | ≒3 | ≒2 | . . . | ≒0 |
| 1 × $10^5$ | | ↓ | ≒1 × $10^3$ | ≒1 × $10^2$ | ≒5 × 10 | ≒1 × 10 | ≒5 | ≒1 | ≒0 | | ≒0 |
| 3 × $10^4$ | Slightly low | | ≒3 × $10^2$ | ≒3 × 10 | ≒2 × 10 | ≒3 | ≒2 | ≒0 | ≒0 | | ≒0 |
| 1 × $10^4$ | | | ≒1 × $10^2$ | ≒1 × 10 | ≒5 | ≒1 | ≒0 | ≒0 | ≒0 | | ≒0 |
| 3 × $10^3$ | | | ≒3 × 10 | ≒3 | ≒2 | ≒0 | ≒0 | ≒0 | ≒0 | | ≒0 |
| 1 × $10^3$ | Low | | ≒1 × 10 | ≒1 | ≒0 | ≒0 | ≒0 | ≒0 | ≒0 | | ≒0 |
| 3 × $10^2$ | | | ≒3 | ≒0 | ≒0 | ≒0 | ≒0 | ≒0 | ≒0 | | ≒0 |
| 1 × $10^2$ | Very low | | ≒1 | ≒0 | ≒0 | ≒0 | ≒0 | ≒0 | ≒0 | | ≒0 |
| 3 × 10 | | | ≒0 | ≒0 | ≒0 | ≒0 | ≒0 | ≒0 | ≒0 | | ≒0 |
| 1 × 10 | | Non-undifferentiated | ≒0 | ≒0 | ≒0 | ≒0 | ≒0 | ≒0 | ≒0 | | ≒0 |
| 0 | | | ≒0 | ≒0 | ≒0 | ≒0 | ≒0 | ≒0 | ≒0 | | ≒0 |

When the minimum detection sensitivity of the LAMP reaction (10 μg of total RNA is subjected to the reaction) is set to 10 copies per reaction, the limit of detection (LOD) of the percentage of undifferentiated cells is 0.0005% (5×$10^{-6}$).

6) However, an LOD comparable to that of 1) above can be obtained through adjustment to further increase the minimum detection sensitivity of the LAMP reaction. When a marker gene is expressed to a slightly low level in undifferentiated cells and is expressed at a very low level (close to zero) in non-undifferentiated cells of interest: (the ratio of the expression level before differentiation to the expression level after differentiation ranges from $10^4$ to $10^5$)

| RNA expression level (copies/μg) per 1 μg of total RNA extracted from cell population in differentiation process | | Differentiation process | Percentage of undifferentiated cells 0.1% 1 × $10^{-3}$ | 0.01% 1 × $10^4$ | 0.005% 5 × $10^{-5}$ | 0.001% 1 × $10^{-5}$ | 0.0005% 5 × $10^{-6}$ | 0.0001% 1 × $10^{-6}$ | 0.00005% 5 × $10^{-7}$ | | 0.00000% |
|---|---|---|---|---|---|---|---|---|---|---|---|
| 3 × $10^4$ | Slightly low | Undifferentiated | ≒3 × $10^2$ | ≒3 × 10 | ≒2 × 10 | ≒3 | ≒2 | ≒0 | ≒0 | . . . | ≒0 |
| 1 × $10^4$ | | ↓ | ≒1 × $10^2$ | ≒1 × 10 | ≒5 | ≒1 | ≒0 | ≒0 | ≒0 | | ≒0 |
| 3 × $10^3$ | | | ≒3 × 10 | ≒3 | ≒2 | ≒0 | ≒0 | ≒0 | ≒0 | | ≒0 |
| 1 × $10^3$ | Low | | ≒1 × 10 | ≒1 | ≒0 | ≒0 | ≒0 | ≒0 | ≒0 | | ≒0 |
| 3 × $10^2$ | | | ≒3 | ≒0 | ≒0 | ≒0 | ≒0 | ≒0 | ≒0 | | ≒0 |
| 1 × $10^2$ | Very low | | ≒1 | ≒0 | ≒0 | ≒0 | ≒0 | ≒0 | ≒0 | | ≒0 |

-continued

| RNA expression level (copies/μg) per 1 μg of total RNA extracted from cell population in differentiation process | Differentiation process | Percentage of undifferentiated cells 0.1% $1 \times 10^{-3}$ | 0.01% $1 \times 10^{4}$ | 0.005% $5 \times 10^{-5}$ | 0.001% $1 \times 10^{-5}$ | 0.0005% $5 \times 10^{-6}$ | 0.0001% $1 \times 10^{-6}$ | 0.00005% $5 \times 10^{-7}$ | 0.00000% |
|---|---|---|---|---|---|---|---|---|---|
| 3 x 10 | | ≒0 | ≒0 | ≒0 | ≒0 | ≒0 | ≒0 | ≒0 | ≒0 |
| 1 x 10 | Non- | ≒0 | ≒0 | ≒0 | ≒0 | ≒0 | ≒0 | ≒0 | ≒0 |
| 0 | undifferentiated | ≒0 | ≒0 | ≒0 | ≒0 | ≒0 | ≒0 | ≒0 | ≒0 |

When the minimum detection sensitivity of the LAMP reaction (10 μg of total RNA is subjected to the reaction) is set to 10 copies per reaction, the limit of detection (LOD) of the percentage of undifferentiated cells is up to 0.005% ($5\times10^{-5}$).

4) When a marker gene is expressed to a very high level in undifferentiated cells, but is expressed at a low level in non-undifferentiated cells of interest: (the ratio of the expression level before differentiation to the expression level after differentiation ranges from $10^4$ to $10^5$)

| RNA expression level (copies/μg) per 1 μg of total RNA extracted from cell population in differentiation process | | Differentiation process | Percentage of undifferentiated cells 0.1% $1 \times 10^{-3}$ | 0.01% $1 \times 10^{-4}$ | 0.005% $5 \times 10^{-5}$ | 0.001% $1 \times 10^{-5}$ | 0.0005% $5 \times 10^{-6}$ | 0.0001% $1 \times 10^{-6}$ | 0.00005% $5 \times 10^{-7}$ | | 0.00000% |
|---|---|---|---|---|---|---|---|---|---|---|---|
| $1 \times 10^{7}$ | Very high | Undifferentiated | ≒$1 \times 10^{5}$ | =$1 \times 10^{4}$ | ≒$8 \times 10^{3}$ | ≒$4 \times 10^{3}$ | ≒$3 \times 10^{\%}$ | ≒$3 \times 10^{3}$ | ≒$3 \times 10^{3}$ | . . . | ≒$3 \times 10^{3}$ |
| $3 \times 10^{6}$ | | ↓ | ≒$3 \times 10^{4}$ | ≒$6 \times 10^{3}$ | ≒$5 \times 10^{3}$ | ≒$3 \times 10^{3}$ | ≒$3 \times 10^{3}$ | ≒$3 \times 10^{3}$ | ≒$3 \times 10^{3}$ | | ≒$3 \times 10^{3}$ |
| $1 \times 10^{6}$ | | | ≒$1 \times 10^{4}$ | ≒$4 \times 10^{3}$ | ≒$3 \times 10^{3}$ | ≒$3 \times 10^{3}$ | ≒$3 \times 10^{3}$ | ≒$3 \times 10^{3}$ | ≒$3 \times 10^{3}$ | | ≒$3 \times 10^{3}$ |
| $3 \times 10^{5}$ | High | | ≒$6 \times 10^{3}$ | ≒$3 \times 10^{3}$ | ≒$3 \times 10^{3}$ | ≒$3 \times 10^{3}$ | ≒$3 \times 10^{3}$ | ≒$3 \times 10^{3}$ | ≒$3 \times 10^{3}$ | | ≒$3 \times 10^{3}$ |
| $1 \times 10^{5}$ | | | ≒$4 \times 10^{3}$ | ≒$3 \times 10^{3}$ | ≒$3 \times 10^{3}$ | ≒$3 \times 10^{3}$ | ≒$3 \times 10^{3}$ | ≒$3 \times 10^{3}$ | ≒$3 \times 10^{3}$ | | ≒$3 \times 10^{3}$ |
| $3 \times 10^{4}$ | Slightly | | ≒$3 \times 10^{3}$ | ≒$3 \times 10^{3}$ | ≒$3 \times 10^{3}$ | ≒$3 \times 10^{3}$ | ≒$3 \times 10^{3}$ | ≒$3 \times 10^{3}$ | ≒$3 \times 10^{3}$ | | ≒$3 \times 10^{3}$ |
| $1 \times 10^{4}$ | low | | ≒$3 \times 10^{3}$ | ≒$3 \times 10^{3}$ | ≒$3 \times 10^{3}$ | ≒$3 \times 10^{3}$ | ≒$3 \times 10^{3}$ | ≒$3 \times 10^{3}$ | ≒$3 \times 10^{3}$ | | ≒$3 \times 10^{3}$ |
| $3 \times 10^{3}$ | | | ≒$3 \times 10^{3}$ | ≒$3 \times 10^{3}$ | ≒$3 \times 10^{3}$ | ≒$3 \times 10^{3}$ | ≒$3 \times 10^{3}$ | ≒$3 \times 10^{3}$ | ≒$3 \times 10^{3}$ | | ≒$3 \times 10^{3}$ |
| $1 \times 10^{3}$ | Low | Non- | ≒$3 \times 10^{3}$ | ≒$3 \times 10^{3}$ | ≒$3 \times 10^{3}$ | ≒$3 * 10^{3}$ | ≒$3 \times 10^{3}$ | ≒$3 \times 10^{3}$ | ≒$3 \times 10^{3}$ | | ≒$3 \times 10^{3}$ |
| $3 \times 10^{2}$ | | undifferentiated | ≒$3 \times 10^{3}$ | ≒$3 \times 10^{3}$ | ≒$3 \times 10^{3}$ | ≒$3 \times 10^{3}$ | ≒$3 \times 10^{3}$ | ≒$3 \times 10^{3}$ | ≒$3 \times 10^{3}$ | | ≒$3 \times 10^{3}$ |

When the minimum detection sensitivity of the LAMP reaction (10 μg of total RNA is subjected to the reaction) is set to $4 \times 10^3$ copies per reaction, the limit of detection (LOD) of the percentage of undifferentiated cells is 0.001% ($1 \times 10^{-5}$).

Unlike the above 1) to 3), a certain amount of the RNA of a marker gene is expressed even in non-undifferentiated cells, so it is necessary to adjust the minimum detection sensitivity of the LAMP reaction. Sensitivity can be adjusted by adjusting various conditions including the reaction composition such as the types and amounts of primers.

5) When a marker gene is expressed to a high level in undifferentiated cells, but is expressed at a low level in non-undifferentiated cells of interest: (the ratio of the expression level before differentiation to the expression level after differentiation ranges from $10^2$ and $10^3$)

| RNA expression level (copies/μg) per 1 μg of total RNA extracted from cell population in differentiation process | | Differentiation process | Percentage of undifferentiated cells 0.1% $1 \times 10^{-3}$ | 0.01% $1 \times 10^{-4}$ | 0.005% $5 \times 10^{-5}$ | 0.001% $1 \times 10^{-5}$ | 0.0005% $5 \times 10^{-6}$ | 0.0001% $1 \times 10^{-6}$ | 0.00005% $5 \times 10^{-7}$ | | 0.00000% |
|---|---|---|---|---|---|---|---|---|---|---|---|
| $3 \times 10^5$ | High | Undifferentiated | ≒$8 \times 10^4$ | ≒$3 \times 10^3$ | ≒$3 \times 10^3$ | ≒$3 \times 10^3$ | ≒$3 \times 10^3$ | ≒$3 \times 10^3$ | ≒$3 \times 10^3$ | . . . | ≒$3 \times 10^3$ |
| $1 \times 10^5$ | | | ≒$4 \times 10^3$ | ≒$3 \times 10^3$ | ≒$3 \times 10^3$ | ≒$3 \times 10^3$ | ≒$3 \times 10^3$ | ≒$3 \times 10^3$ | ≒$3 \times 10^3$ | | ≒$3 \times 10^3$ |
| $3 \times 10^4$ | Slightly low | | ≒$3 \times 10^3$ | ≒$3 \times 10^3$ | ≒$3 \times 10^3$ | ≒$3 \times 10^3$ | ≒$3 \times 10^3$ | ≒$3 \times 10^3$ | ≒$3 \times 10^3$ | | ≒$3 \times 10^3$ |
| $1 \times 10^4$ | | | ≒$3 \times 10^3$ | ≒$3 \times 10^3$ | ≒$3 \times 10^3$ | ≒$3 \times 10^3$ | ≒$3 \times 10^3$ | ≒$3 \times 10^3$ | ≒$3 \times 10^3$ | | ≒$3 \times 10^3$ |
| $3 \times 10^3$ | | | ≒$3 \times 10^3$ | ≒$3 \times 10^3$ | ≒$3 \times 10^3$ | ≒$3 \times 10^3$ | ≒$3 \times 10^3$ | ≒$3 \times 10^3$ | ≒$3 \times 10^3$ | | ≒$3 \times 10^3$ |
| $1 \times 10^3$ | Low | Non- | ≒$3 \times 10^3$ | ≒$3 \times 10^3$ | ≒$3 \times 10^3$ | ≒$3 \times 10^3$ | ≒$3 \times 10^3$ | ≒$3 \times 10^3$ | ≒$3 \times 10^3$ | | ≒$3 \times 10^3$ |
| $3 \times 10^2$ | | undifferentiated | ≒$3 \times 10^3$ | ≒$3 \times 10^3$ | ≒$3 \times 10^3$ | ≒$3 \times 10^3$ | ≒$3 \times 10^3$ | ≒$3 \times 10^3$ | ≒$3 \times 10^3$ | | ≒$3 \times 10^3$ |

When the minimum detection sensitivity of the LAMP reaction (10 μg of total RNA is subjected to the reaction) is set to $4 \times 10^3$ copies per reaction, the limit of detection (LOD) of the percentage of undifferentiated cells is 0.1% ($1 \times 10^{-3}$).

6) When a marker gene is expressed to a slightly low level in undifferentiated cells, and is expressed at a low level in non-undifferentiated cells of interest: (the ratio of the expression level before differentiation to the expression level after differentiation ranges from 10 to $10^2$)

| RNA expression level (copies/μg) per 1 μg of total RNA extracted from cell population in differentiation process | | Differentiation process | Percentage of undifferentiated cells 0.1% $1 \times 10^{-3}$ | 0.01% $1 \times 10^{-4}$ | 0.005% $5 \times 10^{-5}$ | 0.001% $1 \times 10^{-5}$ | 0.0005% $5 \times 10^{-6}$ | 0.0001% $1 \times 10^{-6}$ | 0.00005% $5 \times 10^{-7}$ | | 0.00000% |
|---|---|---|---|---|---|---|---|---|---|---|---|
| $3 \times 10^4$ | Slightly low | Undifferentiated | ≈$3 \times 10^3$ | ≈$3 \times 10^3$ | ≈$3 \times 10^3$ | ≈$3 \times 10^3$ | ≈$3 \times 10^3$ | ≈$3 \times 10^3$ | ≈$3 \times 10^3$ | . . . | ≈$3 \times 10^3$ |
| $1 \times 10^4$ | | | ≈$3 \times 10^3$ | ≈$3 \times 10^3$ | ≈$3 \times 10^3$ | ≈$3 \times 10^3$ | ≈$3 \times 10^3$ | ≈$3 \times 10^3$ | ≈$3 \times 10^3$ | | ≈$3 \times 10^3$ |
| $3 \times 10^3$ | | | ≈$3 \times 10^3$ | ≈$3 \times 10^3$ | ≈$3 \times 10^3$ | ≈$3 \times 10^3$ | ≈$3 \times 10^3$ | ≈$3 \times 10^3$ | ≈$3 \times 10^3$ | | ≈$3 \times 10^3$ |
| $1 \times 10^3$ | Low | Non- | ≈$3 \times 10^3$ | ≈$3 \times 10^3$ | ≈$3 \times 10^3$ | ≈$3 \times 10^3$ | ≈$3 \times 10^3$ | ≈$3 \times 10^3$ | ≈$3 \times 10^3$ | | ≈$3 \times 10^3$ |
| $3 \times 10^2$ | | undifferentiated | ≈$3 \times 10^3$ | ≈$3 \times 10^3$ | ≈$3 \times 10^3$ | ≈$3 \times 10^3$ | ≈$3 \times 10^3$ | ≈$3 \times 10^3$ | ≈$3 \times 10^3$ | | ≈$3 \times 10^3$ |

When the minimum detection sensitivity of the LAMP reaction (10 μg of total RNA is subjected to the reaction) is set to $4\times10^3$ copies per reaction, it is difficult to detect undifferentiated cells even at a percentage of undifferentiated cells of 0.1% ($1\times10^{-3}$).

From the above, in the method of the present invention for detecting the presence or absence of undifferentiated cells in a non-undifferentiated cell population, it is desirable to detect RNA exhibiting a decrease in expression level in the differentiation process, and it is further desirable that the decrease in expression level is a remarkable change. In a test intended for denying the contamination with undifferentiated cells, which requires sensitive detection performance, the higher the expression level of RNA to be detected in undifferentiated cells, the better, and what is more, the lower the expression level of RNA in non-undifferentiated cells, the better. Specifically, the ratio of the RNA expression level in undifferentiated cells to that in non-undifferentiated cells is desirably $10^4$ times or more, more desirably $10^5$ times or more, and most desirably $10^6$ times or more. Further, the RNA expression level in non-undifferentiated cells is desirably $1\times10^4$ copies or less per μg of total RNA level, more desirably $1\times10^3$ copies or less, still more desirably $1\times10^2$ copies or less, even more desirably 1×10 copies or less, and ideally the number of copies is close to zero.

The total quantity of RNA per reaction may be 10 μg or more as long as it is within the range where the minimum detection sensitivity of the LAMP reaction can be controlled, and this value may be increased to 30 μg and 100 μg. At this time, the number of RNA copies of an undifferentiation marker gene per reaction increases by a larger increment in non-undifferentiated cells containing undifferentiated cells than in non-undifferentiated cells containing no undifferentiated cells. Hence, the limit of detection (LOD) of the percentage of undifferentiated cells according to this method can be rendered to have an even higher sensitivity.

Examples of the isothermal nucleic acid amplification method can include the LAMP method, a NASBA method, an SDA method, a TRC method, and an ICAN method. Among these methods, a method like the LAMP method in which nucleic acid amplification is performed with high specificity and efficiently is preferable. Hereinafter, the LAMP method will be described as a specific example, but the method is not particularly limited thereto as long as it is a nucleic acid amplification method having the same features. When nucleic acid amplification is performed targeting RNA by the LAMP method (RT-LAMP method), at least six regions of a nucleic acid (cDNA) synthesized from the template of RNA to be detected are amplified isothermally using at least four different primers, and DNA polymerase having a strand displacement activity (which may hereinafter sometimes be referred to as "strand displacement type DNA polymerase") is used for nucleic acid amplification. The term "strand displacement type DNA polymerase" means a DNA polymerase which, when a double-stranded region is present in the direction of extension during a process of synthesizing a DNA strand complementary to a template DNA, is capable of continuing complementary strand synthesis while dissociating the strand. Further, when a double-stranded region is present in the direction of extension in a process of synthesizing a DNA strand complementary to a template DNA by the strand displacement type DNA polymerase, synthesis of a complementary strand while dissociating the strand is referred to as "strand displacement reaction".

Furthermore, nucleic acid amplification can also be performed by adding one or more primers, for accelerating . . . the reaction (for example, loop primes to be used in the LAMP method).

When the RT-LAMP method is used as the isothermal nucleic acid amplification method in the method of the present invention, in the isothermal nucleic acid amplification method, a nucleic acid synthesized by reverse transcriptase from RNA to be detected serving as a template may be amplified isothermally by a DNA polymerase having strand displacement activity using at least four different primers specifically designed to recognize six distinct regions of the above nucleic acid. When loop primers are used in the RT-LAMP method, a nucleic acid synthesized by reverse transcriptase using RNA to be detected serving as a template may be amplified isothermally by a DNA polymerase having strand displacement activity using at least four different primers specifically designed to recognize six distinct regions of the above nucleic acid as well as one or more additional primers for accelerating the reaction.

The LAMP method, which is one of the isothermal nucleic acid amplification methods, is characterized in that four different primers are specifically designed to recognize six distinct regions of a target gene as shown in FIG. 1 and that reaction is carried out at a constant temperature utilizing a strand displacement reaction. When the target gene is DNA, sample genes, primers, strand displacement type DNA polymerase, substrates, etc. may be kept together at a constant temperature (around 60° C. to 65° C.), whereby a series of treatments from the gene amplification reaction to detection, can be performed in a one-step process. When the target gene is RNA, reverse transcriptase may be added to a reagent from the beginning, whereby amplification and detection can be performed in a one-step process as in the case of DNA (RT-LAMP method).

In the RT-LAMP method, four different primers are designed as shown in FIG. 1 for a sequence that is obtained by replacing U (uracil) in the nucleotide sequence of a target RNA with T (thymine). Specifically, for the target gene, three regions F3c, F2c, and F1c are specified to lie in that order from the 3' end side whereas three regions B1, B2, and B3 are specified on the 5' end side, and four different primers (FIP, F3 Primer, BIP, and B3 Primer) are designed for these six distinct regions. FIP is designed to have an F2 region on the 3'end side which is complementary to the F2c region of the target gene and the same sequence as the F1c region of the target gene on the 5' end side whereas the F3 primer is designed to have an F3 region complementary to the F3c region of the target gene. The BIP and B3 primer on the reverse strand side are designed in the same manner (FIG. 1). Primers can be designed by utilizing PRIMEREXPLORER V5 (Registered Trademark) (primerexplorer.jp/).

The principle of the RT-LAMP method will be described with reference to FIG. 2.

(Reverse Transcription Reaction (RT) Step)

STEP 1 (FIG. 2 (1)): After being prepared, a sample solution is mixed with a reaction solution and the mixture is incubated at 60° C. to 65° C., whereupon BIP anneals to target RNA as shown in FIG. 2 (1) and complementary cDNA is synthesized by reverse transcriptase.

STEP 2 (FIG. 2 (2)): After B3 Primer anneals to the outside of BIP, reverse transcriptase acts to synthesize new complementary cDNA while displacing the cDNA strand previously obtained by extended synthesis from BIP.

STEP 3 (FIG. 2 (3)): FIP anneals to the cDNA that has been brought to a state of single-stranded DNA after extended synthesis from BIP as a result of STEP 2.

(Steps until the formation of a starting structure)

STEP 4 (FIG. 2 (4)): Following the above reverse transcription reaction step (STEP 3, FIG. 2 (3)), the strand displacement type DNA polymerase acts to synthesize a DNA strand complementary to the template of CDNA starting from the 3' end of the F2 region of FIP.

STEP 5 (FIG. 2 (5)): F3 Primer anneals to the outside of FIP and starting from the 3' end, DNA extends while peeling the DNA strand previously synthesized by FIP.

STEP 6 (FIG. 2 (6)): The DNA strand synthesized by F3 Primer and the template DNA form a double-strand DNA.

STEP 7 (FIG. 2 (7)): The DNA strand synthesized by FIP as peeled in the process of STEP 5 (FIG. 2 (5)) has complementary sequences at both ends, so that it self-anneals to form a loop and, hence, a dumbbell-type structure which serves as a starting structure for the LAMP method cycling amplification.

(LAMP Method Cycling Amplification)

STEP 8 (FIG. 2 (8)): First, in the structure of FIG. 2 (7), the DNA strand is extended by DNA synthesis using itself as a template starting from the 3' end of the B1 region, unfolding the loop on the 5' end side. Furthermore, since the B2c region of the loop on the " end side is single-stranded, BIP can anneal thereto, and the DNA strand is extended by DNA synthesis starting from the 3' end of the B2 region while displacing the previously synthesized DNA strand from the B1 region.

STEP 9 (FIG. 2 (9)): Next, in the structure of FIG. 2 (8), the DNA strand as extended from the B1 region that has been brought to a single-stranded state by being peeled by the DNA strand that has been obtained by extended synthesis from BIP has a complementary region on the 3' end and, hence, forms a loop. From the 3' end of the F1 region of this loop, DNA synthesis starts using the single-stranded DNA itself as a template. Then, the resulting DNA strand is extended while displacing the DNA strand from the double-stranded BIP, thus producing a structure shown in FIG. 2 (9).

STEP 10 (FIG. 2 (10)): Through the above process, the DNA strand synthesized from BIP converts to a single strand, and having complementary regions, F1c and F1 as well as B1 and B1c, at opposite ends, it self-anneals to form a loop, producing a structure shown in FIG. 2 (10). The structure of FIG. 2 (10) is completely complementary to the structure of FIG. 2 (7).

STEP 11 (FIG. 2 (11)): In the structure of FIG. 2 (10), DNA synthesis is performed using itself as a template starting from the 3' end of the F1 region as in the case of STEP 7, and furthermore, FIP anneals to the single-stranded F2c region so that DNA synthesis is performed while displacing the DNA strand from F1 region. As a result, a structure shown in FIG. 2 (7) is produced again through the processes of STEPS 10 and 11 in the same manner as the processes of STEPS 7, 8 and 10.

STEP 12 (FIG. 2 (12)): In the structure of FIG. 2 (9) or FIG. 2 (12), FIP (or BIP) anneals to the single-stranded F2c (or B2c) region, thereby synthesizing a DNA strand while displacing the double-stranded portion. As a result of these processes, amplification products are produced in various sizes presenting structures in which complementary sequences are alternately repeated on the same strand.

In the LAMP method, loop primers (FIG. 3) may be additionally designed. The loop primers are primers (Loop primer B and Loop primer F, respectively) each having a sequence complementary to a single-stranded portion of Loop on the 5' end side (between B1 region and B2 region, or F1 region and F2 region) among a dumbbell-like structure that is the starting structure for amplification reaction and a loop structure region to be formed in an amplification product. The use of the loop primers increases the number of the starting points for DNA synthesis, and makes it possible to shorten the time of amplification reaction and improve specificity. The loop primers can be designed by "LAMP method primer design support software PRIMEREXPLORER V5" (Fujitsu "Net Laboratory").

The LAMP method can amplify both DNA and RNA, has extremely high specificity and amplification efficiency, and can perform treatments starting from amplification until detection in a one-step process based on the presence or absence of the formation of the white precipitates of magnesium pyrophosphate as a reaction by-product or the presence or absence of fluorescent color development due to a chelating agent, calcein. In principle, the LAMP method is one of the nucleic acid amplification methods and thus is also capable of distributing a sample into microcompartments for limiting dilution and performing a LAMP reaction in the same manner as in the above digital PCR, and then quantifying a target nucleic acid by a statistical technique (digital LAMP). Further, when an amplification product (characterized by having a stem-loop structure) is synthesized with a target nucleic acid template from a primer that serves as a starting point, the amplification reaction proceeds continuously from the single-stranded loop region under isothermal conditions, and thus it is less susceptible to reaction inhibition due not only to an excess of nucleic acids but also to impurities. Further, in addition to the basic four different primers, a loop primer by which a starting point for the synthesis of a single-stranded loop region of an amplification product is utilized more efficiently may be added to thereby make it possible to increase the amplification efficiency and shorten the amplification reaction. In the present invention, attention is paid to RNA structures such as exons and introns of undifferentiation marker genes whose expression varies significantly in the process of directed differentiation, and thus primers and/or probes for detecting RNA structures that are more abundant in undifferentiated cells than in non-undifferentiated cells can be set.

The use of the LAMP method makes it possible to consecutively perform the reverse transcription of RNA to be detected, its amplification, and then detection of the same. Reverse transcription, amplification and detection can be performed consecutively in one tube. The temperatures for reverse transcription and amplification may be varied, or the temperatures may be unified (for example, 63° C.) to carry out transcription and amplification.

In addition, unlike the PCR method in which the reaction solution volume needs be limited to a small value (5 μL to 100 μL) in order to quickly and accurately control the rise and fall of the reaction temperature in seconds, the LAMP method continuously performs amplification reaction at an isothermal temperature. Hence, in the isothermal nucleic acid amplification method, particularly the LAMP method, sample liquid volume can be increased, and the total quantity of nucleic acids (weight) per test can be 0.5 μg or more. Moreover, the total quantity of nucleic acids (weight) per test can be 5 μg or more, preferably 10.0 μg or more, more preferably 50 μg or more, and most preferably 100.0 μg or more. For example, when the reaction solution volume is set to 5 μL to 100 μL per test as in the PCR method, the total quantity of nucleic acids (weight) is 0.5 μg or more and less than 5 μg. When the reaction solution volume is set to 100 UL to 1,000 μL, the total quantity of nucleic acids is 0.5 μg or more and less than 50 μg. When the reaction solution volume is set to range from 1 mL to 10 mL, the total quantity of nucleic acids is 0.5 μg or more and less than 100 μg. Moreover, when the reaction solution volume is set to 10 mL or more, the total quantity of nucleic acids is 100.0 μg or more. In this manner, the total quantity of nucleic acids can also be increased by increasing the reaction solution volume.

As described in the above section, when the total quantity of nucleic acids (weight) per test is increased, a large amount of nucleic acids other than target nucleic acids are brought into the sample in an increased amount and, at the same time, the sample-derived components (proteins, lipids, sugars, etc.) other than nucleic acids are also brought into the reaction in large quantities. The PCR method is known to be problematic in that the function of polymerase deteriorates due to the depletion of magnesium ions contributing to the structural stabilization of nucleic acid and that the formation of a single-stranded nucleic acid sample is delayed by heat denaturation, whereupon an excess amount of template nucleic acids inhibits the specific amplification reaction. On the other hand, the isothermal nucleic acid amplification method, particularly the LAMP method, is performed under mild heating conditions (around 60° C. to 65° C.) without the need of single-strand formation by heat denaturation and, instead, primers specifically anneal to a plurality of single-stranded regions synthesized in the structure of an amplification product, and a new amplification reaction proceeds from those regions which serve as a starting point for synthesis. Therefore, the method is not easily affected by reaction inhibition due to an excess amount of nucleic acid samples, and is not easily affected by impurities other than nucleic acids. Utilizing these features, it is possible to directly use a sample extract with a low degree of purification for amplification reaction. For example, a culture solution containing a food of interest which is commercially available is used as a reagent for food/environmental test and it is denatured by heating under alkaline conditions, neutralized and simply centrifuged to obtain a supernatant, which can be directly applied as a nucleic acid sample.

Each primer to be used in the present invention has a chain length sufficient to perform binding by base-pairing with a complementary strand while maintaining required specificity under a given environment in various nucleic acid synthesis reactions that constitute the present invention. Specifically, the length of the primer ranges from 5 to 200 bases, and more desirably 10 to 50 base pairs. Since the chain length of a primer that is recognized by a known polymerase that catalyzes a sequence-dependent nucleic acid synthesis reaction is at least about 5 bases, the chain length of an annealing portion needs to be greater than that. In addition, in order to expect specificity as a nucleotide sequence, it is stochastically desirable to use a length of 10 or more bases. On the other hand, it is difficult to prepare an unduly long nucleotide sequence by chemical synthesis, so the above-mentioned chain length is given as an example of a length within a desirable range. Note that the chain length given here as an example is just the chain length of the portion that anneals to a complementary strand. Speaking of FIP, it is composed of at least two regions, F2 and F1c. Therefore, the chain length given here as an example should be understood as the chain length of each region that constitutes the primer.

The thus amplified nucleic acid can be detected using turbidity, fluorescence, electrophoresis, etc.

Magnesium pyrophosphate is produced as a by-product in the process of nucleic acid amplification reaction. Since this by-product is produced in proportion to the amplified product, it is observed as white turbid in the LAMP method which yields a very large amount of amplified products. Therefore, the presence or absence of a target gene can be confirmed by the presence or absence of white turbid. Turbidity can be measured with a turbidity meter.

The thus amplified nucleic acid can also be detected using fluorescence. Typical fluorescence detection methods include a method using an intercalator and a method using a fluorescently labeled probe; either or both of these methods may be used and, alternatively, another detection method may be used. For the intercalator method, SYTO63, ethidium bromide, SYBR (registered trademark) Green, SYBR (registered trademark) Gold, Oxazole Yellow, Thiazole Orange, PicoGreen, GelGreen and the like can be used. There are many types of fluorescently labeled probes, as exemplified by Qprobe (registered trademark), TaqMan (registered trademark) probe, MolecularBeacon, cycling probe and the like. In many cases of using fluorescently labeled probes, a fluorescent substance is combined with a quencher for detection based on the FRET principle. A fluorescent substance absorbs light of a specific wavelength to become excited and emits light of a wavelength different from the wavelength of the absorbed light when it returns to the initial ground state. Quenchers receive light energy from fluorescent substances and emit it as light or thermal energy. Examples of fluorescent substances can include FITC, TMR, 6-joe, Bodipy (registered trademark)—FL/C6, Bodipy (registered trademark)—FL/C3, TAMRA, FAM, and HEX. Examples of quenchers can include BHQ (registered trademark)—1, and BHQ (registered trademark)—2. Qprobe is a quenching probe and requires no quencher. In Qprobe, fluorescence resonance energy transfer occurs when guanine is present in the vicinity of a base complementary to a base modified with a fluorescent dye upon hybridization, and the fluorescence is quenched. Examples of the fluorescent dye possessed by Qprobe include FITC, TMR, 6-joe, Bodipy (registered trademark)—FL/C6, and Bodipy (registered trademark)—FL/C3.

A probe to be used in the present invention has a chain length sufficient to perform binding by base-pairing with a complementary strand while maintaining required specificity under a given environment. The chain length of the probe is not particularly limited, but specifically ranges from preferably 5 to 50 bases, and more preferably 10 to 40 bases.

The LAMP method has such a feature that an extremely large amount of nucleic acids is synthesized and a large amount of pyrophosphate ions is also produced as a by-product. When a chelating agent, calcein, is used as a fluorescence visual detection reagent, calcein binds with manganese ions to quench fluorescence before amplification, but emits fluorescence as the LAMP reaction proceeds to generate pyrophosphate ions and deprive manganese ions. Furthermore, the pyrophosphate ions bind with magnesium ions in the reaction solution to emit enhanced fluorescence. According to this principle, the presence or absence of amplification by the LAMP reaction can be easily determined visually based on the presence or absence of fluorescent color development.

In detection by electrophoresis, a nucleic acid amplification reaction solution may, for example, be electrophoresed with about 2% agarose and stained with a staining reagent such as ethidium bromide or SYBR (registered trademark) Green I etc., to allow for observation of a electrophoresis pattern.

According to the method of the present invention, the differentiation state of cells at the time of directed differentiation and/or after directed differentiation from undifferentiated cells to differentiated cells can be evaluated.

In the present invention, non-undifferentiated cells may be differentiated cells. Non-differentiated cells can be differentiated cells derived from pluripotent stem cells such as human or non-human mammalian induced pluripotent stem cells (iPS cells) and embryonic stem cells (ES cells); alternatively, they can be cultured cells that are not limited to the differentiated cells derived from the pluripotent stem cells. Specific examples of such cultured cells that are not limited to the differentiated cells derived from the pluripotent stem cells specifically include, but are not particularly limited to, HEK293T cells (www.wikiwand.com/ja/HEK293 cells), Hela cells (ja.wikipedia.org/wiki/Hela cells) and HUVEC cells (www.wikiwand.com/en/Human_umbilical_vein_endothelial_cel 1). When the non-undifferentiated cells are differentiated cells derived from pluripotent stem cells, the presence or absence of residual cells (undifferentiated cells) in an undifferentiated state at the time of or after directed differentiation of the non-undifferentiated cells can be detected with high sensitivity according to the present invention. On the other hand, when non-undifferentiated cells are cultured cells that are not limited to the differentiated cells derived from pluripotent stem cells, the presence or absence of undifferentiated cells contaminating the cultured cell population can be detected with high sensitivity by the present invention. For example, contamination with undifferentiated cells on equipment used in cell processing facilities handling multiple types of cells or in automatic cell culture equipment, particularly cross-contamination with undifferentiated cells in differentiated cells of the same individual [such phenomena cannot be analyzed by SNPs (single-base polymorphism)] can be effectively detected.

In the method of the present invention, RNA the amount of which in a sample containing undifferentiated cells in a non-undifferentiated cell population is equal to or higher than the detection limit of the isothermal nucleic acid amplification method, and the amount of which in non-undifferentiated cells is equal to or below the detection limit of the isothermal nucleic acid amplification method may be detected and when the RNA is detected in the sample, the result may be determined to be positive, and when the RNA is not detected in the sample, the result may be determined to be negative.

The limit of detection can be, for example, less than 10 copies in X μg of RNA purified from non-undifferentiated cells. X is the maximum RNA weight as determined to be negative when RNA purified from non-undifferentiated cells is detected by RT-LAMP using a system in which a sample to which RNA to be detected is added in an amount of 100 copies/test and a sample to which RNA to be detected is added in an amount of 10 copies/test are determined to be positive in a test by RT-LAMP, and a sample to which RNA to be detected is added in an amount of 5 copies/test is determined to be negative in the same test. When undifferentiated cells are to be detected with high sensitivity, X is preferably 1 or more, more preferably 10 or more, and even more preferably 100 or more.

X can be appropriately set according to the amount of RNA to be detected and should be one that enables correct determination of positive or negative bordering a detection limit. For example, in the case of testing a sample prepared from a state in which undifferentiated cells are present in non-undifferentiated cells, if RNA that is not expressed at all in non-undifferentiated cells is subjected to detection, a result that can be correctly determined as positive is obtainable by increasing the quantity of RNA even when the expression level is not very high in undifferentiated cells.

In the present invention, the percentage of undifferentiated cells in a non-undifferentiated cell population can be 0.1% or less, 0.05% or less, 0.025% or less, 0.01% or less, 0.005% or less, 0.0025% or less, 0.001% or less, and 0.0001% or less.

The present invention also provides a kit for detecting the presence or absence of undifferentiated cells in a non-undifferentiated cell population, comprising a reagent with which RNA derived from an undifferentiation marker gene exhibiting a significant difference in expression level between the undifferentiated cells and the non-undifferentiated cells can be detected by an isothermal nucleic acid amplification method.

A reagent with which RNA derived from an undifferentiation marker gene exhibiting a significant difference in expression level between undifferentiated cells and non-undifferentiated cells can be detected by an isothermal nucleic acid amplification method may comprise primers. To detect amplified nucleic acids, the reagent may further comprise a probe and/or a colorimetric reagent. The functions and configurations etc., of the primers and probes are as described above. The probe may be fluorescently labeled. The colorimetric reagent may be any substance that enables detection of amplified nucleic acids, and examples thereof can include magnesium ions that produce magnesium pyrophosphate enabling turbidity measurement, calcein as a fluorescence visual detection reagent, and ethidium bromide and SYBR Green I, which are staining reagents to be used in electrophoresis.

The kit may further comprise a reagent required for nucleic acid amplification: substrates (4 types of bases: dGTP, dCTP, dATP, dTTP), magnesium ions (for example, magnesium chloride), buffer, potassium ions, etc.), enzymes for nucleic acid amplification (DNA polymerase (for example, strand displacement type DNA polymerase), reverse transcriptase, etc.), distilled water, RNA for positive control and primers for amplification thereof, a fluorescent probe for detection, and the like.

The reagent to be contained in the kit of the present invention may be in a dry state. In that case, a dried reagent may, for example, be preliminarily fixed in a reaction tube (bottom, lid, etc.) and just before use, a primer solution and a sample solution are added to the reaction tube so that the dried reagent is dissolved in these solutions, and then a nucleic acid amplification reaction is performed.

EXAMPLES

Hereinbelow, the present invention will be described more specifically with reference to the following Examples. However, the scope of the present invention is not limited to these Examples.

Example 1

In the process of directed differentiation of iPS cells into hepatocytes, cells at the stage of differentiation into hepatic endoderm cells (hereinafter, HE cells) were defined as non-undifferentiated cells, into which iPS cells (undifferentiated cells) were spiked-in (mixed) to prepare a dilution series. Using the dilution series as samples, the minimum value of the percentage of undifferentiated cells spiked-in (mixed) in a non-undifferentiated cell population obtained by the qRT-PCR method was examined. Note that LINC00678 was selected as an undifferentiation marker gene to be detected.

Method for Preparing Samples

1. Each type of cells was treated according to Cell Rep. 2017 Dec. 5; 21 (10): 2661-2670.

2. After iPS cells were differentiated to HE cells by 10 days of directed differentiation, the latter were collected using Trypsin-EDTA (Gibco) to prepare an HE cell suspension.
3. The iPS cells maintaining an undifferentiated state were collected using Accutase (ICT) to prepare an iPS cell suspension.
4. After measuring the number of cells of each type, the iPS cell suspension was spiked-in (mixed) into the HE cell suspension; in such a manner that the iPS cells would have the "spiked-in iPS cell percentage" shown in FIG. 4, thereby preparing a sample.
5. Each sample was centrifuged to remove the supernatant and from the resulting cell precipitate, RNA was purified using the PureLink RNA Mini Kit (Invitrogen).
6. The concentration of the purified RNA was quantified using Nanodrop 2000c (Thermo Fisher Scientific).
7. Using the purified RNA as a template, cDNA was synthesized using a High Capacity cDNA Reverse Transcription Kit (Thermo Fisher Scientific).

qRT-PCR Method

RT-PCR Primerprobe for Detection of LINC00678

RT-PCR primer/probe for detection of LINC00678

| Type | | Nucleotide sequence (5'→3') | |
|---|---|---|---|
| Primer | Fw | CATCTCACCAATTTTAAATCAGGAC | (SEQ ID NO: 1) |
| | Bw | CTCCCGTCATTCTGCTAACAC | (SEQ ID NO: 2) |
| Probe | | Universal Probe Library Probe 017 (Roche) | |

[qRT-PCR Reaction Protocol]

Two-step: RT-PCR was performed on the cDNA obtained by a process up to step 7 of the above method for preparing samples. Using THUNDERBIRD Probe qPCR Mix (TOYOBO CO., LTD.), the above primers and probe as well as LightCycler480 (Roche.), a qRT-PCR reaction was performed, and then the gene expression level was quantified by the AACp method using 18S rRNA (ABI) as an internal standard. The final quantity of RNA in this reaction was 12:5 ng/test, thereby preparing a reaction solution.

This test was repeated 5 times, and a significant difference test was performed by t-test between each sample containing spiked-in iPS cells and a sample containing no spiked-in iPS cells. With the significance level of 5%, a spiked-in iPS cell percentage that was one-stage higher than the maximum spiked-in iPS cell percentage determined to have no significant difference was set as the limit of detection (LOD).

[Result]

As shown in FIGS. 4(*a*) and 4(*b*), the LOD of the qRT-PCR method was 0.05%.

| Spiked-in iPSC percentage (%) | Average expression level | Standard deviation | P value | Test result |
|---|---|---|---|---|
| 5.0000% | 1.2E−06 | 4.6E−07 | 0.0069 | ** |
| 2.5000% | 7.9E−07 | 4.0E−07 | 0.0148 | * |
| 1.0000% | 3.0E−07 | 1.4E−07 | 0.0040 | ** |
| 0.5000% | 1.6E−07 | 7.6E−08 | 0.0053 | ** |
| 0.2500% | 6.4E−08 | 2.7E−08 | 0.0033 | ** |
| 0.1000% | 3.3E−08 | 1.0E−08 | 0.0008 | ** |
| 0.0500% | 1.9E−08 | 1.1E−08 | 0.0102 | * |
| 0.0250% | 8.9E−09 | 8.2E−09 | 0.0724 | No |
| 0.0100% | 5.0E−09 | 4.2E−09 | 0.1363 | significant |
| 0.0050% | 4.0E−10 | 8.9E−10 | 0.1516 | difference |
| 0.0025% | 3.9E−09 | 4.0E−09 | 0.2377 | |
| 0.0010% | 7.4E−10 | 1.7E−09 | 0.2107 | |
| 0.0000% | 2.2E−09 | 3.3E−09 | 0.5000 | |

A significant level of 5% (P value < 0.05) and a significant level of 1% (P value < 0.01) as determined by t-test are denoted as "*" and "**", respectively.

Example 2

As in Example 1, cells at the stage of differentiation into HE cells were defined as non-undifferentiated cells, into which iPS cells were spiked-in (mixed) to prepare a dilution series to be used as samples for detection of undifferentiated cells, and then the detection results were compared between the RT-LAMP method and the qRT-PCR method. The undifferentiation marker gene to be detected was LINC00678 as in Example 1.

In the RT-LAMP method, the LAMP primer set was designed using PRIMEREXPLORER V5 (set 1), and RT-LAMP including a reverse transcription reaction was performed using the RNA obtained by a process up to step 6 of the above method for preparing samples.

The test was conducted by performing qRT-PCR in the same manner as in Example 1 (final quantity of RNA was 12.5 ng/test).

RT-LAMP Method

The nucleotide sequences of each primer and a probe used are shown below.

RT-LAMP Primer/Probe for Detection of LINC00678 (Set 1)

| RT-LAMP primer/probe for detection of LINC00678 (set 1) | | | |
|---|---|---|---|
| Type | | Nucleotide sequence (5'→3') | |
| Primer | F3 | GACGGGAGTGTGAGATCC | (SEQ ID NO: 3) |
| | B3 | AGATCTTCTCCTGAATCCTCAG | (SEQ ID NO: 4) |
| | FIP | TTGGAAATAGTTCTCGGTTGCTCTCCACATGGCGAGGCAC | (SEQ ID NO: 5) |
| | BIP | TGGTCAGGTGGAGTAAAACATAAGGAGACACCTCCATGCTGTC | (SEQ ID NO: 6) |
| | LoopF | CAAGAAGAAAACAGGTTCCTGG | (SEQ ID NO: 7) |
| | LoopB | GGTTCAAAGCATGAAAAAAATTGG | (SEQ ID NO: 8) |
| Probe | | BODIPY(Fluorescent dye)-CCTTCACTTTGAGCCAGGCAATGGTCAG-Pi(Phosphoric acid) | (SEQ ID NO: 9) |

[RT-LAMP Reaction Protocol]

1. For the RNA obtained by a process up to step 6 of the above method for preparing samples, a reaction solution was prepared at the final quantity of RNA of 1.0 μg/test.
2. Using Lightcycler480 (Roche), a reverse transcription reaction was performed at 55° C. for 10 minutes, followed by a LAMP amplification reaction at 63° C. for 90 minutes, with the fluorescence intensity of the probe being measured in real time at 20-second intervals. Fluorescence intensity was measured at 465/510 nm.
3. The time when the difference in fluorescence intensity from the initial value became −1 after the start of the device was taken as Tt value. When Tt value was less than 90 minutes, the result was determined as "LAMP reaction occurring", and when Tt value was 90 minutes or more, the result was determined as "no LAMP reaction occurring". Each sample was tested multiple times (N=2) at the same time. The sample with a result of "LAMP reaction occurring" in all of the multiple tests was determined to be positive (indicated by o in the table below), and the sample with a result of "no LAMP reaction occurring" in all of the multiple tests was determined to be negative (indicated by x in the table below).

| Concentration of each reagent per RT-LAMP reaction (final concentration after addition of RNA sample) | |
|---|---|
| Reagent | Final concentration |
| Dextran | 1.5% |
| Tricine | 10 mM |
| MgSO4 | 8 mM |
| dNTPs | 1.4 mM |
| DTT | 1 mM |
| Tween20 | 0.2% |
| FCP | 1% |
| KCl | 30 mM |
| SYTO63 | 0.188 μM |
| Warmstart Bst | 9 U |
| Warmstart RTx | 1.5 U |
| Probe | 0.04 μM |
| F3 and B3 | 0.2 μM each |
| FIP and BIP | 1.6 μM each |
| LoopF and/or LoopB | 0.8 μM each |

Results

In the qRT-PCR method, a spiked-in iPS cell percentage one-stage higher than the maximum spiked-in iPS cell percentage determined to be undetectable was set as the limit of detection (LOD). In the RT-LAMP method, a spiked-in iPS cell percentage one-stage higher than the maximum spiked-in iPS cell percentage determined to be negative in all cases was set as the limit of detection (LOD).

As a result, the LOD of the qRT-PCR method was 0.005% which was more sensitive than that of Example 1 whereas the LOD of the RT-LAMP method was 0.0025% which was even more sensitive. Further, the weight of nucleic acids in a sample per test subjected to this LAMP reaction was 1.0 μg exceeding 500 ng (0.5 μg) or the guide for the upper limit in a typical PCR reaction, but it was well detectable.

| Number of HE cells | Number of iPS cells | Spiked-in iPS cell percentage (%) | RT-LAMP | qRT-PCR |
|---|---|---|---|---|
| $1.0 \times 10^6$ | 0 | 0 | x | N.D. |
| $1.0 \times 10^6$ | 25 | 0.000025 | o | N.D. |
| $1.0 \times 10^6$ | 50 | 0.00005 | o | $4.0 \times 10^{-9}$ |
| $1.0 \times 10^6$ | 100 | 0.0001 | o | $1.4 \times 10^{-10}$ |
| $0.2 \times 10^6$ | 100 | 0.0005 | o | $4.5 \times 10^{-8}$ |

o: "LAMP reaction occurring" in all tests (N = 2).
x: "no LAMP reaction occurring" in all tests (N = 2).
N.D.: Not Detected
Numerical values in qRT-PCR results represent gene expression levels as determined by the ΔΔCp method using 18S rRNA as the internal standard.

Example 3

As in [Example 2], cells at the stage of differentiation into HE cells (endodermal tissue) were defined as non-undifferentiated cells, and in addition, cells at the stage of differentiation into EC cells (vascular endothelial cells, mesodermal tissue) were also defined as non-undifferentiated cells, and into these two types of cells, iPS cells were spiked-in (mixed) to prepare a dilution series for use as samples for detection of undifferentiated cells, and then the detection of undifferentiated cells was tested by the RT-LAMP method.

An undifferentiation marker gene to be detected in the dilution series using HE cells was LINC00678 as in Examples 1 and 2, but a different LAMP primer set (set 2) was designed as compared with the primer set used in Example 2. On the other hand, ESRG was selected as an undifferentiation marker gene to be detected in the dilution series using EC cells and primers/probe set was designed accordingly.

In the RT-LAMP method, RT-LAMP including a reverse transcription reaction was performed using the RNA obtained by a process up to step 6 of the above method for preparing samples.

RT-LAMP Method

The nucleotide sequences of each primer and a probe used are shown below.

RT-LAMP Primer/Probe (Set 2) for Detection of LINC00678

RT-LAMP primer/probe for detection of LINC00678 (set 2)

| Type | | Nucleotide sequence (5'→3') | |
|---|---|---|---|
| Primer | F3 | CCCTGTCCTCCTGTTCTT | (SEQ ID NO: 10) |
| | B3 | CAGGAGCTGATTCTGTTGC | (SEQ ID NO: 11) |
| | FIP | GTTCGTTGGGCTGGTCGGCTCCGTGAGAAAGATCCACCTA | (SEQ ID NO: 12) |
| | BIP | AAATCAGGACCTACCAGTCTGCCCGTCTCGCAGGGTATCAGTC | (SEQ ID NO: 13) |
| | LoopB | TGCTCATACTTGATCTGGATGA | (SEQ ID NO: 14) |
| Probe | | AGGTCCTCAGACCGACCAGCCC-BODIPY(Fluorescent dye) | (SEQ ID NO: 15) |

RT-LAMP Primer Probe for Detection of ESRG

RT-LAMP primer/probe for detection of ESRG

| Type | | Nucleotide sequence (5'→3') | |
|---|---|---|---|
| Primer | F3 | GGAACTCTGGCCCAAGGT | (SEQ ID NO: 16) |
| | B3 | CTGTGTGAAGAGACCACCAA | (SEQ ID NO: 17) |
| | FIP | TTCTGAGGCGATCAGGCAGCCTCCTTCTTGGCTTACTGGC | (SEQ ID NO: 18) |
| | BIP | GCAGACCATCATGGACGCCGAGGCTTTGTGTGAGCAACA | (SEQ ID NO: 19) |
| | LoopB | GCTTTAGCCCGCCTGCA | (SEQ ID NO: 20) |
| Probe | | GCCTGCACCCAGGTGAAATAAACAGCC-BODIPY(Fluorescent dye) | (SEQ ID NO: 21) |

[RT-LAMP Reaction Protocol]

1. For the RNA obtained by a process up to step 6 of the above method for preparing samples, a reaction solution was prepared at the final quantity of RNA of 5.0 μg/test.
2. The concentrations of the respective reagents per RT-LAMP reaction (final concentrations after addition of RNA sample) were the same as the conditions described in [Example 2] except that the concentrations of the substrates and enzymes were varied for different primer/probe sets: 1.4 mM dNTPs, 3 U Warmstart Bst, and 3 U Warmstart RTx for LIN00678 (set 2), and 0.9 mM dNTPs, 9 U Warmstart Bst, and 1.5 U Warmstart RTx for ESRG.
3. After reverse transcription reaction at 55° C. for 10 minutes using Lightcycler480 (Roche), LAMP amplification reaction was performed for 90 minutes at reaction temperatures off 67° C. for LINC00678 (set 2) and 63° C. for ESRG, with the fluorescence intensity of the probe being measured in real time at 20-second intervals. Fluorescence intensity was measured at 465/510 nm.
4. The time when the difference in fluorescence intensity from the initial fluorescence became −1 after the start of the device was taken as Tt value, and when Tt value was less than 90 minutes, the result was determined as "LAMP reaction occurring", and when Tt value was 90 minutes or more, the result was determined as "no LAMP reaction occurring". Each sample was tested multiple times (N=2) at the same time. The sample with a result of "LAMP reaction occurring" in all of the multiple tests was determined to be positive (indicated by o in the table below), and the sample with a result of "no LAMP reaction occurring" in all of the multiple tests was determined to be negative (indicated by x in the table below).

Results

The LODs of the two RT-LAMP methods were 0.00003% for LINC00678 (set 2) and 0.00032% for ESRG, demonstrating sensitivities about $10^2$ to $10^3$ or more times higher than the LOD of RT-PCR in Example 2. Those two RT-LAMP methods targeted the same undifferentiation marker gene, LINC00678, and yet they exhibited higher sensitivities than when set 1 was used. This is due not only to optimization of reaction conditions including the designing of primers and a detection probe but also to the result of increasing the weight of nucleic acids in a sample per test to 5.0 μg. This indicates that even if the amount of contaminating nucleic acids increases, a small amount of a nucleic acid containing a specific sequence to be detected can be detected adequately.

Furthermore, even those cells which had been differentiated from iPS cells but which exhibited different cell functions from HE cells (hepatic endoderm cells) and EC cells (vascular endothelial cells) could also be tested by RT-LAMP to allow for detection of a trace amount of spiked-in iPS cells in those differentiated cells.

Spike-in experiment into each non-undifferentiated cell (HE cell/EC cell)

| Spiked-in iPSC percentage (%) | LINC00678 (set 2) | ESRG |
|---|---|---|
| 0.00000% | x | x |
| 0.00003% | ○ | x |
| 0.00010% | ○ | x |
| 0.00032% | ○ | ○ |
| 0.00100% | ○ | ○ |
| 0.00317% | ○ | ○ |
| 0.01000% | ○ | ○ |
| Final quantity of RNA | 5.0 μg/test | 5.0 μg/test |

○: "LAMP reaction occurring" in all of multiple measurements (N = 2).
x: "no LAMP reaction occurring" in all of multiple measurements (N = 2).
LINC00678: iPS cells were spiked-in into HE cells.
ESRG: iPS cells were spiked-in into EC cells.

Example 4

HEK293T cells (ectodermal tissue (Non-Patent Document No. 7)) of human embryonic kidney cell clone or Hela cells of human cervical cancer-derived cells, both being cultured cells but not differentiated cells derived from pluripotent stem cells, were used as non-undifferentiated cells, into which iPS cells were spiked-in (mixed) to prepare a diluted series for use as samples, and then the detectability of undifferentiated cells was tested by the RT-LAMP method as in Examples 1, 2 and 3.

As undifferentiation marker genes to be detected, not only LINC00678 which was the same as in Examples 1, 2 and 3 but also SFRP2, CNMD, USP44 and LIN28A were selected.

As the RT-LAMP primer/probe set for LINC00678, set 1 and set 2 described above were used. With the use of these sets and newly designed primer.probe sets for SFRP2, CNMD, USP44 and LIN28A, a total of 6 types of RT-LAMP were compared for their detection sensitivity.

RT-LAMP Primer/Probe for Detection of SFRP2

RT-LAMP primer/probe for detection of SFRP2

| Type | | Nucleotide sequence (5'→3') | |
|---|---|---|---|
| Primer | F3 | TCCAAAGGTATGTGAAGCCT | (SEQ ID NO: 22) |
| | B3 | TCATGTCCTCACAGGTGC | (SEQ ID NO: 23) |
| | FIP | TCTCGGTTGATGTAGGTTATCTCCTTGACAACGACATAATGGAAACGC | (SEQ ID NO: 24) |
| | BIP | TGGAGACCAAGAGCAAGACCATTTGTCTTTGAGCCACAGCAC | (SEQ ID NO: 25) |
| | LoopB | TTTACAAGCTGAACGGTGTGTC | (SEQ ID NO: 26) |
| Probe | | GGTGTGTCCGAAAGGGACCTGAAGAAATC-BODIPY(Fluorescent dye) | (SEQ ID NO: 27) |

RT-LAMP Primer/Probe for Detection of CNMD

RT-LAMP primer/probe for detection of CNMD

| Type | | Nucleotide sequence (5'→3') | |
|---|---|---|---|
| Primer | F3 | AGTGGTAAGAAAAATTGTTCCA | (SEQ ID NO: 28) |
| | B3 | ACAGATTCCTTCGTGATCC | (SEQ ID NO: 29) |
| | FIP | ACTGGGTCTGGTTTCATTATTCAGTAAAAAGACCACACAGTGGAC | (SEQ ID NO: 30) |
| | BIP | CAAGAGGACTCACAAGCCTTCGTCTAGGGTCGAATGTCAT | (SEQ ID NO: 31) |
| | LoopB | CAGCAGGAAGGGGAAAGCA | (SEQ ID NO: 32) |
| Probe | | CTTCCAGCGCCTGGGTTGCTCC-BODIPY(Fluorescent dye) | (SEQ ID NO: 33) |

RT-LAMP Primer/Probe for Detection of USP44

RT-LAMP primer/probe for detection of USP44

| Type | | Nucleotide sequence (5'→3') | |
|---|---|---|---|
| Primer | F3 | CCGCCAGGACTTTTCACT | (SEQ ID NO: 34) |
| | B3 | AGCTGAGAAATGCATAATCCAA | (SEQ ID NO: 35) |
| | FIP | TAACTCAGAGGTCAGTCCCTGTAGGAGATCAGCATTTGCCCTG | (SEQ ID NO: 36) |
| | BIP | CCAAAGGCCGACCTGGGGAAAGTCTCTGTTCACAACACTTG | (SEO ID NO: 37) |
| | LoopF | GGATCGCCCAGTTTCCAT | (SEQ ID NO: 38) |
| Probe | | BODIPY(Fluorescent dye)-CTGATTTTGAGGTTTTAATAGTTTTCAGATGCTT-Pi(Phosphoric acid) | (SEQ ID NO: 39) |

RT-LAMP Primer/Probe for Detection of LIN28A

| RT-LAMP primer/probe for detection on LIN28A | | | |
|---|---|---|---|
| Type | | Nucleotide sequence (5'→3') | |
| Primer | F3 | TTCCTGTCCATGACCGC | (SEQ ID NO: 40) |
| | B3 | TCCTTTTGGCCGCCTCT | (SEQ ID NO: 41) |
| | FIP | TCCGGAACCCTTCCATGTGCAGCGACCCCCCAGTGGATGTC | (SEQ ID NO: 42) |
| | BIP | AGTTCACCTTTAAGAAGTCAGCCACACTCCCAATACAGAATACTCC | (SEQ ID NO: 43) |
| | LoopB | AGGGTCTGGAATCCATGCG | (SEQ ID NO: 44) |
| Probe | | GGAATCCATCCGTGTCACCGGACC-BODIPY(Fluorescent dye) | (SEQ ID NO: 45) |

Method for Preparing Samples

1. HEK293T cells and Hela cells were individually cultured and collected to prepare respective cell suspensions.
2. Undifferentiated iPS cells were collected using Accutase (ICT) to prepare an iPS cell suspension.
3. After measuring the number of each type of cells, the iPS cell suspension was spiked-in (mixed) into the respective cell suspensions of HEK293T cells and HeLa cells at the "spiked-in iPS cell percentage" indicated in the table below, thereby preparing samples.
4. Each sample was centrifuged to remove the supernatant and RNA was purified from the resulting cell precipitates using a PureLink RNA Mini Kit (Invitrogen).
5. The concentration of purified RNA was quantified using Nanodrop 2000c (Thermo Fisher Scientific).

[RT-LAMP Reaction Protocol]

1. The concentrations of the respective reagents per RT-LAMP reaction (final concentrations after addition of RNA sample) were the same as the conditions described in [Example 2] except that the concentrations of the substrate and enzymes were varied for different primer/probe sets: 1.4 mM dNTPs, 3 U Warmstart Bst, and 3 U Warmstart RTx for SFRP2 and LIN28A, and 0.9 mM dNTPs, 9 U Warmstart Bst, and 1.5 U Warmstart RTx for CNMD and USP44. The conditions for LIN00678 set 1 and LIN00678 set 2 were the same as those shown in [Example 2] and [Example 3], respectively.
2. RNA obtained by a process up to step 5 of the above method for preparing samples was subjected to reverse transcription reaction at 55° C. for 10 minutes using Lightcycler480 (Roche) and, thereafter, LAMP amplification reaction was performed for 90 minutes at 63° C. (LINC00678 set 1, CNMD, USP44, LIN28A) or 65° C. (SFRP2) or 67° C. (LINC00678 set 2), with the fluorescence intensity of the probe being measured in real time at 20-second intervals. Fluorescence intensity was measured at 465/510 nm.
3. The time when the difference in fluorescence intensity from the initial fluorescence became −1 after the start of the device was taken as Tt value, and when Tt value was less than 90 minutes, the result was determined as "LAMP reaction occurring", and when Tt value was 90 minutes or more, the result was determined as "no LAMP reaction occurring". Each sample was tested multiple times (N=2) at the same time. The sample with a result of "LAMP reaction occurring" in all of the multiple tests was determined to be positive (indicated by o in the table below), and the sample with a result of "no LAMP reaction occurring" in all of the multiple tests was determined to be negative (indicated by x in the table below). The sample with a result of "LAMP reaction occurring" in one of the multiple tests was denoted by A in the table below.

Results

| Spike-in experiment into HEK293T cells | | | | | |
|---|---|---|---|---|---|
| Spiked-in iPSC percentage (%) | LINC00678 (set 1) | LINC00678 (set 2) | SFRP2 | SFRP2 | CNMD |
| 0.00000% | x | x | x | x | x |
| 0.00003% | | | | Δ | |
| 0.00010% | | Δ | | ○ | |
| 0.00025% | | Δ | Δ | | |
| 0.00032% | | | | ○ | |
| 0.00050% | Δ | Δ | Δ | | ○ |
| 0.00100% | ○ | ○ | ○ | ○ | ○ |
| 0.00250% | ○ | ○ | ○ | | |
| 0.00317% | | | | ○ | |
| 0.00500% | | | | | ○ |
| 0.01000% | | | | ○ | ○ |
| Final quantity of RNA | 10.0 μg/test | 1.0 μg/test | 1.0 μg/test | 5.0 μg/test | 3.0 μg/test |

○: "LAMP reaction occurring" in all of multiple measurements (N = 2).
Δ: "LAMP reaction occurring" in one of multiple measurements (N = 2).
x: "no LAMP reaction occurring" in all of multiple measurements (N = 2).

Each blank column indicates that no experiment was conducted.

Spike-in experiment that involves spiking into Hela cells

| Spiked-in iPSC percentage (%) | LINC00678 (set 2) | USP44 | LIN28A |
|---|---|---|---|
| 0.00000% | x | x | x |
| 0.00003% | | | Δ |
| 0.00010% | | | Δ |
| 0.00032% | ○ | ○ | ○ |
| 0.00100% | ○ | ○ | ○ |
| 0.00317% | ○ | ○ | ○ |
| 0.01000% | ○ | ○ | ○ |
| Final quantity of RNA | 5.0 μg/test | 5.0 μg/test | 5.0 μg/test |

○: "LAMP reaction occurring" in all of multiple measurements (N = 2).
Δ: "LAMP reaction occurring" in one of multiple measurements (N = 2).
x: "no LAMP reaction occurring" in all of multiple measurements (N = 2).

In the iPS cell spike-in experiment into HEK293T cells, LINC00678 (set 1) exhibited LOD of 0.001% (RNA final quantity of 10.0 μg), LINC00678 (set 2) exhibited LOD of 0.001% (RNA final quantity of 1.0 μg), and SFRP2 exhibited LOD of 0.001% (RNA final quantity of 1.0 μg) and LOD of 0.0001% (RNA final quantity of 5.0 μg), and CNMD exhibited LOD of 0.0005% (RNA final quantity of 3.0 μg). In the iPS cell spike-in experiment into HeLa cells, all of LINC00678 (set 2), USP44 and LIN28A exhibited LOD of 0.00032% (RNA final quantity of 5.0 μg).

In whichever types of the non-undifferentiated cells used in the experiment and the undifferentiation marker genes selected as the detection targets, high detection sensitivity was confirmed as demonstrated by LODs of 0.001% to 0.0001%. Particularly in the case of SFRP2, it was demonstrated that LOD could be improved by increasing the quantity of RNA using the same primer/probe set. Regarding the types of non-undifferentiated cells, the usefulness of the present method was confirmed using the cells classified as endoderm/mesoderm in Example 3 and those classified as ectoderm in Example 4. From these results, it is considered that the non-undifferentiated cells may be any population of differentiated cells, including endodermal, mesodermal or ectodermal lineages.

Example 5

In the spike-in experiments described in the above examples, known amounts of undifferentiated cells were added. Unlike these experiments, differentiated cells obtained by directed differentiation from undifferentiated cells through culturing were used and an examination was conducted to see whether or not the undifferentiated cells which were not differentiated as expected and which remained as residual undifferentiated cells could be detected with high sensitivity. HE cells were used as iPS cell-derived differentiated cells.

When iPS cell clones obtained by less than about 35 passages (referred to as "normal clones") which are generally recommended for use in the art are differentiated into HE cells in the culture condition described in the specification, no or extremely few undifferentiated cells maintain an undifferentiated state. Hence, in this Example, not only a normal clone but also an iPS cell clone obtained by 35 or more passages (referred to as "over-passaged cell clone") was used as an iPS cell clone in which undifferentiated cells are likely to remain (Non-Patent Document No. 8). The number of residual undifferentiated cells in the differentiated HE cells was confirmed by the culture amplification method (Non-Patent Document No. 3).

[Culture Amplification Method]

Using a normal cell clone and an over-passaged cell clone, HE cell suspensions were prepared as in [Example 1], followed by RNA purification and test by the RT-LAMP method. In addition, portions of the cell suspensions were collected and seeded at $1.6\times10^5$ cells/well in StemFit medium (Ajinomoto) supplemented with ROCK inhibitor (Wako Pure Chemical Industries) using laminin-coated 24-well plates; thereafter, cells were cultured at 37° C. with daily exchange of medium with StemFit medium until colonies of undifferentiated cells were formed.

One week later, in order to detect undifferentiated cell colonies, immunostaining was performed using an anti-SOX2 antibody or an anti-OCT4A antibody (Cell Signaling Technologies) as the primary antibody against a pluripotency marker, and a fluorescently labeled secondary antibody capable of detecting the primary antibody (Thermo Fisher Scientific). Based on the images obtained by immunostaining, the number of positive colonies was counted and then divided by the number of seeded cells to calculate the residual rate of undifferentiated cells.

Note that immunostaining was performed according to the following procedure.

Cells were fixed by treatment with 4% paraformaldehyde for 15 minutes. After washing twice with PBS, cell membranes were permeabilized with 0.1% TRITONX-100 in PBS (PBST) for 10 minutes and subsequently blocked with 5% FBS in PBST. After one hour, the blocking buffer was removed. An appropriately diluted solution of the primary antibodies was added and cells were treated at 4° C. overnight. Then, cells were washed three times with PBS. Diluted solution of the secondary antibodies was applied and the mixture was allowed to stand for one hour at room temperature under shade conditions. In the last step, cells were washed three times with PBS, followed by addition of Apathy's Mounting Media (Wako Pure Chemical Corporation) for observation. An all-in-one fluorescence microscope BZ-X710 (KEYENCE) was used for observation, and the green fluorescence of the whole-well image was photographed with a 4× objective lens. The number of colonies was visually counted based on the acquired images.

[RT-LAMP Reaction Protocol]

As the undifferentiation marker genes to be detected, not only ESRG and LINC00678 (set 2) which were the same as in Example 3 but also PRDM14 was selected.

The newly designed primer/probe set for PRDM14 is shown below.

RT-LAMP primer/probe for detection of PRDM14

| | Type | Nucleotide sequence (5'→3') | |
|---|---|---|---|
| Primer | | TCGGTTCCAGTTCACGG | (SEQ ID NO: 46) |
| | B3 | GACTTCACCAAACACCGTC | (SEQ ID NO: 47) |
| | FIP | ATGGTGCAGGCTGGCTGGGGGAGGACCTGCACTTCGTT | (SEQ ID NO: 48) |
| | BIP | TCCCCCCAGACAGCTCTGGCATAGACCTTCTGGAAGTTGAA | (SEQ ID NO: 49) |
| | LoopF | TGCTCCAGGCTGGGAGTGAC | (SEQ ID NO: 50) |
| | LoopB | ATCTGATTCTCTTCCTCAAACTCTG | (SEQ ID NO: 51) |
| Probe | | TTCTCTTCCTCAAACTGTGGATAAAGACTCCC-BODIPY(Fluorescent dye) | (SEQ ID NO: 52) |

1. For the RNA obtained by a process up to step 6 of the above method for preparing samples, a reaction solution was prepared at the final quantity of RNA of 1.0 µg/test.
2. The concentrations of the respective reagents per RT-LAMP reaction of PRDM14 (final concentrations after addition of RNA sample) were the same as the conditions described in [Example 2] except that the concentrations of the substrate and enzymes were varied: 0.6 mM dNTPs, 9 U Warmstart Bst, and 1.5 U Warmstart RTx. Note that the conditions for LIN00678 set 2 and ESRG were the same as those shown in [Example 3], respectively.
3. After reverse transcription reaction at 55° C. for 10 minutes using Lightcycler480 (Roche), LAMP amplification reaction was performed for 90 minutes at reaction temperatures of 67° C. for LINC00678 (set 2) and 63° C. for ESRG and PRDM14, with the fluorescence intensity of the probe was measured in real time at 20-second intervals. Fluorescence intensity was measured at 465/510 nm.
4. The time when the difference in fluorescence intensity from the initial fluorescence became −1 after the start of the device was taken as Tt value. When Tt value was less than 90 minutes, the result was determined as "LAMP reaction occurring", and when Tt value was 90 minutes or more, the result was determined as "no LAMP reaction occurring". Each sample was tested multiple times (N=2) at the same time. The sample with a result of "LAMP reaction occurring" in all of the multiple tests was determined to be positive (indicated by o in the table below), and the sample with a result of "no LAMP reaction occurring" in all of the multiple tests was determined to be negative (indicated by x in the table below).

Results

| iPS cell clone used | Undifferentiated cell residual rate based on culture amplification method. | LINC00678 (set 2) | ESRG | PRDM14 |
|---|---|---|---|---|
| Normal cell clone | 0.0000% | x | x | x |
| Over-passaged cell clone Lot. 1 | 0.0016% | ○ | ○ | ○ |
| Over-passaged cell clone Lot. 2 | 0.0016% | ○ | ○ | ○ |
| Over-passaged cell clone Lot. 3 | 0.0028% | ○ | ○ | ○ |
| Over-passaged cell clone Lot. 4 | 0.0038% | ○ | ○ | ○ |
| Over-passaged cell clone Lot. 5 | 0.0044% | ○ | ○ | ○ |
| Over-passaged cell clone Lot. 6 | 0.0119% | ○ | ○ | ○ |
| Over-passaged cell clone Lot. 7 | 0.0330% | ○ | ○ | ○ |
| Over-passaged cell clone Lot. 8 | 0.0391% | ○ | ○ | ○ |
| Over-passaged cell clone Lot. 9 | 0.0481% | ○ | ○ | ○ |
| Over-passaged cell clone Lot. 10 | 0.0538% | ○ | ○ | ○ |
| Over-passaged cell clone Lot. 11 | 0.0547% | ○ | ○ | ○ |
| Over-passaged cell clone Lot. 12 | 0.0619% | ○ | ○ | ○ |
| Over-passaged cell clone Lot. 13 | 0.0828% | ○ | ○ | ○ |
| Over-passaged cell clone Lot. 14 | 0.0969% | ○ | ○ | ○ |
| Over-passaged cell clone Lot. 15 | 0.1184% | ○ | ○ | ○ |
| Over-passaged cell clone Lot. 16 | 0.2445% | ○ | ○ | ○ |
| Over-passaged cell clone Lot. 17 | 0.4119% | ○ | ○ | ○ |
| Over-passaged cell clone Lot. 18 | 0.4159% | ○ | ○ | ○ |
| Final quantity of RNA | | 1.0 µg/test | 1.0 µg/test | 1.0 µg/test |

○: "LAMP reaction occurring" in all of multiple measurements (N = 2).

x: "no LAMP reaction occurring" in all of multiple measurements (N = 2).

For HE cells derived from the normal iPS cell clone, no residual undifferentiated cells were detected by the culture amplification method. On the other hand, for HE cells derived from over-passaged iPS cell clones, trace amounts of residual undifferentiated cells were detected by the culture amplification method. RNA was extracted from the cell suspensions that gave the above results in the culture amplification method and used as a sample for testing by the RT-LAMP method. The result obtained from RNA as a test sample for which no residual undifferentiated cells were detected by the culture proliferation method was determined to be negative, and the result obtained from RNA as a test sample for which residual undifferentiated cells were detected by the culture amplification method was determined to be positive in all cases.

Example 6

In the nucleic acid amplification reaction based on an enzymatic reaction, the reaction rate varies not only with the reaction composition conditions including substrate concentration and enzyme activity but also with reaction conditions such as temperature, so that the amount of a template nucleic acid that can be amplified within a certain period of time also varies. Similarly, in the isothermal nucleic acid amplification methods used in the present invention, particularly the LAMP method, the detection sensitivity is varied by changing the reaction composition conditions including the nucleotide sequences of primers to be used, the amount of the primers, and the concentrations of substrates, enzymes, catalysts therefor, and the like. An examination was made to see whether or not this phenomenon could be used to test the amount of a template nucleic acid contained in a specimen.

Method for Preparing Samples

An artificial gene (SEQ ID NO: 53) containing a nucleotide sequence which can be amplified by the RT-LAMP primer/probe (set 2) for detection of LINC00678 as shown in [Example 3] above was used as a sample. From the artificial gene quantified by absorbance measurement, a serial dilution series having 0 to 1,000 copies per test was prepared and subjected to the following RT-LAMP reaction.

[RT-LAMP Reaction Protocol]

1. A plurality of amplification reaction solutions were prepared by varying only the concentration of dNTPs as a substrate from 0.4 mM to 1.4 mM among the concentrations of reagents per RT-LAMP reaction (final concentrations after sample spike-in) using the RT-LAMP primer/probe (set 2) for detection of LINC00678 shown in [Example 2] above.
2. The serial dilution series of the artificial gene as prepared by the above method for preparing samples were added to the respective amplification reaction solutions and, thereafter, a LAMP amplification reaction was performed at 67° C. for 90 minutes using Lightcycler480 (Roche), with the fluorescence intensity of the probe being measured in real time at 20-second intervals. Fluorescence intensity was measured at 465/510 nm.
3. The time when the difference in fluorescence intensity from the initial fluorescence became −1 after the start of the device was taken as Tt value. When Tt value was less than 90 minutes, the result was determined as "LAMP reaction occurring", and when Tt value was 90 minutes or more, the result was determined as "no LAMP reaction occurring". Each sample was tested multiple times (N=2) at the same time. The sample with a result of "LAMP reaction occurring" in all of the multiple tests was determined to be positive (indicated by o in the table below), and the sample with a result of "no LAMP reaction occurring" in all of the multiple tests was determined to be negative (indicated by x in the table below).

Results

Sensitivity adjustment by varying dNTPs concentration (LINC00678 set2 RT-LAMP)

| Copy number (copies/test) | dNTPs 1.4 mM | 1.2 mM | 1.0 mM | 0.8 mM | 0.6 mM |
|---|---|---|---|---|---|
| 0 | x | x | x | x | x |
| 10 | ○ | ○ | x | x | x |
| 100 | ○ | ○ | ○ | ○ | x |
| 1000 | ○ | ○ | ○ | ○ | ○ |

○: "LAMP reaction occurring" in all of multiple measurements (N = 2).
x: "no LAMP reaction occurring" in all of multiple measurements (N = 2).

As the concentration of the substrates, dNTPs, decreases, more copies of the artificial gene are needed to give a result that can be determined as positive. This indicates that detection sensitivity can be easily adjusted by changing the concentration of the substrates, dNTPs, which are one of the reaction compositions.

By utilizing such a difference in detection sensitivity due to the difference among various reaction conditions, the amount of a template nucleic acid contained in a sample can be quantified.

For example, the amount of a template nucleic acid present in each sample can be quantified as follows: when the same sample with an unknown LINC00678 RNA copy number is subjected to reaction using LINC00678 RT-LAMP (set 2) reaction composition including 3 different dNTPs concentrations, [1] 1.2 mM, [2] 1.0 mM, and [3] 0.6 mM, Case 1) 1000 copies or more of LINC00678 RNA are present in the sample subjected to the reaction when the sample is determined to be positive under all of the conditions [1], [2] and [3], or Case 2) 10 or more copies and less than 1000 copies of LINC00678 RNA are present in the sample subjected to the reaction when the sample is determined to be positive only under the conditions [1] and [2], or Case 3) 10 or more copies and less than 100 copies of LINC00678 RNA are present in the sample subjected to the reaction when the sample is determined to be positive only under the condition [1].

Example 7

The above [Example 6] was a test using the artificial gene. In this Example, the amounts of undifferentiated cells were quantified under such conditions that undifferentiated cells were spiked-in (mixed) in non-undifferentiated cells as in [Example 3] and [Example 4].

Method for Preparing Samples

1. Hela cells were cultured and collected to prepare a cell suspension.
2. Those iPS cells which maintained an undifferentiated state were collected using Accutase (ICT) to prepare iPS cell suspensions.
3. After measuring the numbers of the respective cells, the iPS cell suspension was spiked-in (mixed) into the HeLa cell suspension at the "spiked-in iPS cell percentage" indicated in the table below, thereby preparing various samples.

4. Each sample was centrifuged to remove the supernatant and RNA was purified from the resulting cell precipitates using a PureLink RNA Mini Kit (Invitrogen).
5. The concentration of the purified RNA was quantified using Nanodrop 2000c (Thermo Fisher Scientific).

[RT-LAMP Reaction Protocol]

1. Two amplification reaction solutions were prepared by varying only the concentration of the substrates dNTPs to be 0.8 mM and 0.9 mM, respectively among the concentrations of reagents per RT-LAMP reaction (final concentrations after sample spike-in) using the RT-LAMP primer/probe for detection of USP44 shown in [Example 4] above.
2. RNA obtained by the process up to step 5 of the above method for preparing samples was subjected to reverse transcription reaction at 55° C. for 10 minutes using Lightcycler480 (Roche) and LAMP amplification reaction was performed for 90 minutes at 63° C., with the fluorescence intensity of the probe being measured in real time at 20-second intervals. Fluorescence intensity was measured at 465/510 nm.
3. The time when the difference in fluorescence intensity from the initial fluorescence became −1 after the start of the device was taken as Tt value. When Tt value was less than 90 minutes, the result was determined as "LAMP reaction occurring", and when Tt value was 90 minutes or more, the result was determined as "no LAMP reaction occurring". Each sample was tested multiple times (N=2) at the same time. The sample with a result of "LAMP reaction occurring" in all of the multiple tests was determined to be positive (indicated by o in the table below), and the sample with a result of "no LAMP reaction occurring" in all of the multiple tests was determined to be negative (indicated by x in the table below).

Results

Sensitivity adjustment by varying dNTPs concentration (USP44 RT-LAMP experiment on iPS cells spiked-into HeLa cells)

| Spiked-in iPSC percentage (%) | dNTPs 0.9 mM | dNTPs 0.8 mM |
|---|---|---|
| 0.00000% | x | x |
| 0.00032% | x | x |
| 0.00100% | ○ | x |
| 0.00320% | ○ | ○ |
| 0.01000% | ○ | ○ |

○: "LAMP reaction occurring" in all of multiple measurements (N = 2).
x: "no LAMP reaction occurring" in all of multiple measurements (N = 2).

As in [Example 6], the reaction sensitivity varies as the concentration of substrates dNTPs decreases and, hence, more spiked-in iPS cells need to ensure the occurrence of an amplification reaction. By utilizing such a difference in detection sensitivity due to differences among various reaction conditions, the amount of undifferentiated cells that are contained in a non-undifferentiated cell population can be detected.

For example, when the same sample having an unknown percentage of undifferentiated cells (iPS cells) was subjected to reaction using USP44 RT-LAMP reaction composition including two different concentrations of dNTPs, [1] 0.9 mM and [2] 0.8 mM, the amount of undifferentiated cells can be detected as follows:

Case 1) the percentage of undifferentiated cells is 0.0032% or more when amplification occurs under both conditions [1] and [2];

Case 2) the percentage of undifferentiated cells is 0.001% or more and less than 0.0032% when amplification occurs only under condition [1]; and Case 3) the percentage of undifferentiated cells is less than 0.001% when no amplification occurs under condition [1] or [2].

Discussion

The LODs of the undifferentiation marker gene LINC00678 in qRT-PCR ranged from 0.05% to 0.005% whereas that in the LAMP method according to the present invention ranged from 0.00032% to 0.00003%, showing higher detection sensitivity. The undifferentiation marker gene to be detected should be selected from those which exhibit such a quantitative change that their expression level decreases in the process of differentiation. It should be noted that a versatile marker gene should be selected without being limited to a particular undifferentiation marker gene as shown in the foregoing Examples using a number of genes. Further, the non-undifferentiated cells in which undifferentiated cells may potentially be present are not limited to those differentiated and/or derived from pluripotent stem cells (human ES cells, human iPS cells, etc.) and somatic stem cells and they may be cells isolated from somatic cells such as HEK293T cells and HeLa cells.

For detecting the presence or absence of undifferentiated cells in the present invention, it is preferable that nucleic acid samples derived from cell populations that may potentially contain undifferentiated cells are used in as large amounts as possible, so a method that is limited in the volume of a reaction solution and the amount of nucleic acids to be used is not preferable. In general, PCR is susceptible to reaction inhibition in the presence of an excess amount of nucleic acids, so in order to detect a trace amount of iPS cells in a sample by PCR, their percentage must be relatively high by all means. On the other hand, in the LAMP method, even when the final quantity of RNA is in an excess amount ranging from 1 μg to 10 μg, satisfactory amplification reactions occur and the detection sensitivity is high, so the LAMP method is suitable as a method for detecting residual undifferentiated cells. Further, the undifferentiation marker gene to be selected as a detection target in the present method is preferably a gene having not only high RNA expression level in undifferentiated cells but also low RNA expression level in differentiated cells. As mentioned above, in the present method, the marker gene is not limited to any particular type, and the non-undifferentiated cells which may potentially contain undifferentiated cells are also not limited to any specific types and, hence, the present method should be recognized as versatile.

Further, in the isothermal nucleic acid amplification methods to be used in the present invention, particularly in the LAMP method, detection sensitivity can be adjusted from 10 copies/test to several thousands of copies/test by varying the reaction composition conditions including the nucleotide sequences of primers to be used, the amounts of the primers, the concentrations of substrates, enzymes, catalysts therefor, and the like. In other words, detection sensitivity is variable depending on various conditions involved in the reaction. This characteristic allows the detection of presence, absence, or amount of undifferentiated cells by preparing multiple reaction composition conditions for providing different detection sensitivities and subjecting one sample to tests under such various reaction composition conditions. Note that multiple reaction composition conditions for providing different detection sensitivities are not limited in any detail and may be set for each reaction vessel (tube) or may be in such a form that tests can be performed simultaneously under multiple reaction conditions in a single device which yet has branched internal flow paths.

Reference Example 1

LINC00678 and PRDM14 as Undifferentiated Cell Marker Genes

For the purpose of extracting marker genes serving as indicators of iPS cells, microarray analysis of mice at their development stage and single-cell RNA sequence analysis in the directed differentiation process of iPS cell-derived hepatocytes were performed to search for genes that were specifically expressed at high levels in undifferentiated iPS cells but which were expressed at low levels in differentiated cells.

Results

Among multiple candidate genes, LINC00678 (FIG. 5) and PRDM14 (FIG. 6) were extracted as genes that were expressed by qRT-PCR at high levels in iPS cells but which were expressed at lower levels in differentiated cells such as iPS cell-derived definitive endoderm cells (DE) and hepatic endoderm cells (HE).

All publications, patents and patent applications cited herein are incorporated herein by reference in their entirety.

INDUSTRIAL APPLICABILITY

The present invention can be used for highly sensitive detection of the presence or absence of residual cells in an undifferentiated state (undifferentiated cells) during or after directed differentiation from undifferentiated cells into differentiated cells. The present invention can also be used for highly sensitive detection of the presence or absence of undifferentiated cells in a cultured cell population of cells not limited to differentiated cells derived from pluripotent stem cells.

The invention claimed is:

1. A method for detecting RNA from undifferentiated cells in a cell population of interest, the method comprising detecting, by an isothermal nucleic acid amplification method, RNA from an undifferentiation marker gene in a sample containing a nucleic acid derived from the cell population of interest, wherein the RNA from the undifferentiation marker gene satisfies:

(i) a ratio of an RNA expression level in the undifferentiated cells to an RNA expression level in non-undifferentiated cells is $10^4$ or more times, and/or (ii) the RNA expression level in the non-undifferentiated cells is $1\times10^4$ copies or less per μg of a total RNA level.

2. The method according to claim 1, wherein the undifferentiated cells are pluripotent stem cells or somatic stem cells.

3. The method according to claim 1, wherein the method further comprises determining a presence of the RNA to be detected in the sample in an amount equal to or higher than a limit of detection of the isothermal nucleic acid amplification method and in the non-undifferentiated cells in an amount equal to or below the limit of detection of the isothermal nucleic acid amplification method.

4. The method according to claim 1, wherein the detecting comprises synthesizing and amplifying a nucleic acid from the RNA isothermally using at least four different primers specifically designed to recognize six distinct regions on a target sequence.

5. The method according to claim 1, wherein the nucleic acid is amplified by DNA polymerase having strand displacement activity.

6. The method according to claim 5, wherein the nucleic acid is synthesized by reverse transcriptase from the RNA and amplified isothermally with the DNA polymerase having strand displacement activity using at least four different primers specifically designed to recognize six distinct regions on a target sequence.

7. The method according to claim 4, wherein the nucleic acid amplification is performed further using one or more additional primers for further accelerating a reaction.

8. The method according to claim 7, wherein the nucleic acid is synthesized by reverse transcriptase from the RNA and amplified isothermally with a DNA polymerase having strand displacement activity using at least four different primers specifically designed to recognize six distinct regions on the target sequence, as well as one or more additional primers for further accelerating the reaction.

9. The method according to claim 1, wherein a reverse transcription of the RNA to be detected to amplification and the detection of RNA are consecutively performed.

10. The method according to claim 1, wherein the RNA derived from the undifferentiation marker gene satisfies (i) the ratio of the RNA expression level in the undifferentiated cells to the RNA expression level in the non-undifferentiated cells is $10^4$ or more times.

11. The method according to claim 1, wherein the RNA derived from the undifferentiation marker gene satisfies (ii) the RNA expression level in the non-undifferentiated cells is $1\times10^4$ copies or less per μg of the total RNA level.

12. The method according to claim 1, wherein the RNA derived from the undifferentiation marker gene satisfies (i) the ratio of the RNA expression level in the undifferentiated cells to the RNA expression level in the non-undifferentiated cells is $10^4$ or more times and (ii) the RNA expression level in the non-undifferentiated cells is $1\times10^4$ copies or less per μg of the total RNA level.

13. The method according to claim 1, wherein the isothermal nucleic acid amplification method is a LAMP method.

14. The method according to claim 1, wherein the undifferentiated cells are pluripotent stem cells.

15. The method according to claim 1, wherein the undifferentiated cells are somatic stem cells.

16. The method according to claim 1, wherein the undifferentiation marker gene comprises at least one selected from the group consisting of SFRP2, CNMD, USP44, CNMD, LIN28A, SOX2, OCT4, NANOG, TDGF1, and TNFRSF8.

17. The method according to claim 1, wherein the undifferentiation marker gene comprises LINC00678.

18. The method according to claim 1, wherein the undifferentiation marker gene comprises PRDM14.

19. The method according to claim 1, wherein the undifferentiation marker gene comprises ESRG.

20. The method according to claim 1, wherein the undifferentiation marker gene comprises at least one selected from the group consisting of SFRP2, CNMD, and USP44.

21. The method according to claim 1, wherein the undifferentiation marker gene comprises at least one selected from the group consisting of NANOG and TNFRSF8.

22. The method according to claim 1, wherein the undifferentiation marker gene comprises at least one selected from the group consisting of LINC00678, ESRG, SFRP2, CNMD, USP44, NANOG, and TNFRSF8.

* * * * *